(12) United States Patent
Reyes Gil et al.

(10) Patent No.: US 12,260,329 B2
(45) Date of Patent: Mar. 25, 2025

(54) IDENTIFYING NEUTROPHIL EXTRACELLULAR TRAPS IN PERIPHERAL BLOOD SMEARS

(71) Applicant: MONTEFIORE MEDICAL CENTER, Bronx, NY (US)

(72) Inventors: Morayma Reyes Gil, New Rochelle, NY (US); Kenji Ikemura, Bronx, NY (US); Mohammad Barouqa, Bronx, NY (US); Henny Billett, Bronx, NY (US); Margarita Kushnir, Bronx, NY (US)

(73) Assignee: MONTEFIORE MEDICAL CENTER, Bronx, NY (US)

( * ) Notice: Subject to any disclaimer, the term of this patent is extended or adjusted under 35 U.S.C. 154(b) by 291 days.

(21) Appl. No.: 17/597,371

(22) PCT Filed: Jul. 31, 2020

(86) PCT No.: PCT/US2020/044514
§ 371 (c)(1),
(2) Date: Jan. 4, 2022

(87) PCT Pub. No.: WO2021/022165
PCT Pub. Date: Feb. 4, 2021

(65) Prior Publication Data
US 2022/0254015 A1      Aug. 11, 2022

Related U.S. Application Data

(60) Provisional application No. 62/881,272, filed on Jul. 31, 2019.

(51) Int. Cl.
*G06N 3/00*      (2023.01)
*G01N 33/49*    (2006.01)
(Continued)

(52) U.S. Cl.
CPC ............ *G06N 3/08* (2013.01); *G01N 33/491* (2013.01); *G06N 3/04* (2013.01); *G06T 7/0012* (2013.01);
(Continued)

(58) Field of Classification Search
CPC ............ G06N 3/08; G06N 3/04; G06N 3/045; G06N 3/063; G01N 33/491; G01N 1/30;
(Continued)

(56) References Cited

U.S. PATENT DOCUMENTS 5,315,512 A        5/1994  Roth
10,303,923 B1 *    5/2019  Parise ................. G06V 10/454
(Continued)

FOREIGN PATENT DOCUMENTS

WO        2018/213840 A1    11/2018

OTHER PUBLICATIONS

Sheeba et al, Detection of poor quality peripheral blood smear images used in detection of leukocytes and erythrocytes, Fourth International Conference on Image Information Processing (ICIIP), pp. 1-4 (Year: 2017).*

(Continued)

*Primary Examiner* — Xiao Liu
(74) *Attorney, Agent, or Firm* — Perkins Coie LLP

(57) ABSTRACT

The present technology is directed to identifying neutrophil extracellular traps (NETs) in blood. For example, the present technology provides artificial intelligence systems, architectures, and/or programs that can rapidly and/or automatically identify and/or enumerate NETs in peripheral blood smears, CBC scattergrams, and the like. The artificial intelligence architectures can be integrated into current automated imaging and/or analysis systems (e.g., automated imaging systems for performing cell blood counts (CBC)). The artificial (Continued)

intelligence architectures can also be integrated into another computing device, such as a mobile device.

27 Claims, 18 Drawing Sheets

(51) Int. Cl.
  *G06N 3/04* (2023.01)
  *G06N 3/08* (2023.01)
  *G06T 7/00* (2017.01)
  *G06T 7/11* (2017.01)
  *G06V 10/44* (2022.01)
  *G06V 10/77* (2022.01)
  *G06V 10/82* (2022.01)
  *G06V 10/84* (2022.01)
  *G06V 20/69* (2022.01)

(52) U.S. Cl.
  CPC .............. *G06T 7/11* (2017.01); *G06V 10/454* (2022.01); *G06V 10/7715* (2022.01); *G06V 10/82* (2022.01); *G06V 10/84* (2022.01); *G06V 20/698* (2022.01); *G06T 2207/20084* (2013.01); *G06T 2207/30024* (2013.01); *G06V 2201/03* (2022.01)

(58) Field of Classification Search
  CPC ................ G06T 7/0012; G06T 7/11; G06T 2207/20084; G06T 2207/30024; G06V 10/454; G06V 10/7715; G06V 10/82; G06V 10/84; G06V 20/698; G06V 2201/03; G06F 18/24133
  See application file for complete search history.

(56) References Cited

U.S. PATENT DOCUMENTS

| | | |
|---|---|---|
| 10,430,946 B1 * | 10/2019 | Zhou .................. A61B 5/02007 |
| 2017/0343537 A1 * | 11/2017 | Kono ................. G01N 15/1429 |
| 2019/0114511 A1 | 4/2019 | Gao et al. |
| 2019/0147313 A1 | 5/2019 | Geissinger et al. |
| 2019/0220704 A1 * | 7/2019 | Schulz-Trieglaff ......................... G06F 18/2431 |

OTHER PUBLICATIONS

International Search Report and Written Opinion for PCT/US2020/44514, Nov. 24, 2020, 13 pages.

Howard, et al. "MobileNets: Efficient Convolutional Neural Networks for Mobile Vision Applications" arXiv, Apr. 17, 2017 9 pages.

Ginely, et al. "Computational detection and quantification of human and mouse neutrophil extracellular traps in flow cytometry and confocal microscopy," Scientific Reports, Dec. 19, 2017, 11 pages.

* cited by examiner

IDENTIFYING NEUTROPHIL EXTRACELLULAR TRAPS IN PERIPHERAL BLOOD SMEARS

CROSS-REFERENCE TO RELATED APPLICATION(S)

This application is a 371 National Phase Application of PCT Application No. PCT/US2020/044514 entitled "IDENTIFYING NEUTROPHIL EXTRACELLULAR TRAPS IN BIOLOGICAL SAMPLES" filed on Jul. 31, 2020, which claims priority to U.S. Provisional Application No. 62/881,272, filed on Jul. 31, 2019, the disclosure of which is hereby incorporated by reference herein in its entirety.

TECHNICAL FIELD

The present technology generally relates to identifying and/or enumerating neutrophil extracellular traps (NETs), and in particular to identifying and/or enumerating NETs in blood or other biological samples using, for example, peripheral blood smears, flow cytometry, cell blood count (CBC) scattergrams, and the like.

BACKGROUND

Neutrophils are a common white blood cell that are part of the innate immune system, regulating immunity through phagocytosis, generation of reactive oxygen species (ROS), and degranulation. Neutrophils can also form neutrophil extracellular traps ("NETs") in a process known as netosis. NETs are composed of extracellular decondensed chromatin networks, and are generated by neutrophils to engulf and kill pathogens. NETs have been found to form during infection, inflammation, and thrombosis. Despite their key role in immunity, it is difficult to detect, characterize, and enumerate NETs using conventional technologies.

Many acute conditions, such as sepsis and thrombosis, pose significant risks to patients. Sepsis, a systemic inflammatory response to an infection, can be particularly life threatening. For example, the systemic inflammatory response in sepsis can cause multi-organ dysfunction, multi-organ failure, shock, and/or death. More than 1.7 million Americans develop sepsis every year, and approximately 270,000 die due to sepsis. In cases of severe sepsis such as septic shock, the mortality rate can be as high as 80%. Moreover, one third of hospital deaths are attributed to sepsis.

DETAILED DESCRIPTION

Figure 1A:
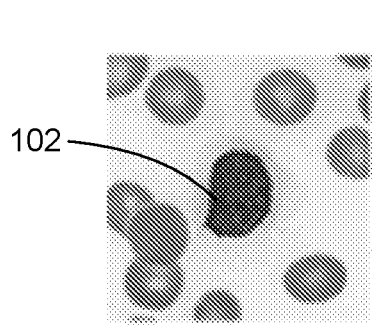
FIGS. 1A-1F are images of Wright Giemsa stained biological samples including degenerating lymphocytes in accordance with embodiments of the present technology.
Figure 1B:
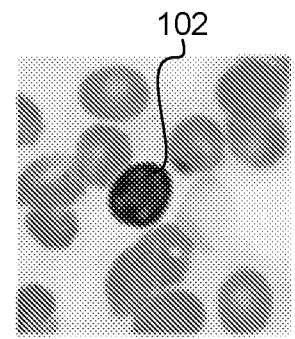
Figure 1C:
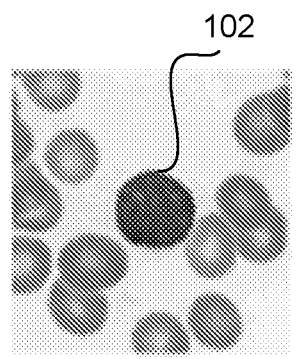
Figure 1D:
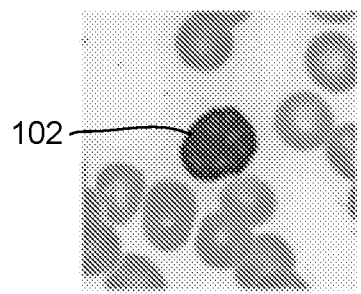

The present technology generally provides systems, devices, and methods for identifying neutrophil extracellular traps (NETs). In some embodiments, the present technology provides systems, devices, and methods for identifying and/or enumerating NETs in blood or other biological samples using, for example, peripheral blood smears, flow cytometry, CBC scattergrams, and the like. In some embodiments, the present technology provides artificial intelligence systems, architectures, and/or programs that can rapidly and/or automatically identify and/or enumerate NETs in peripheral blood smears. The artificial intelligence architectures can be integrated into current automated imaging and/or analysis systems (e.g., automated imaging systems for performing cell blood counts (CBC)). The artificial intelligence architecture can also be integrated into another computing device, such as a mobile device. In some embodiments, the identification of NETs in blood can be used to diagnose a patient with a pathological condition.

As provided above, some embodiments of the present technology include identifying NETs in a blood sample. For example, certain methods in accordance with the present technology include obtaining and/or receiving a biological sample including blood from a patient. The biological sample can be obtained using standard techniques, such as venipuncture or finger-prick. The obtained sample can be stained using one or more standard staining techniques, such as antibodies for flow cytometry and Wright Giemsa for histological staining. Once stained, a user or data analysis module can analyze the morphological features of the stained sample to determine whether the sample contains NETs.

As provided above, some embodiments of the present technology include artificial intelligence architectures that can automatically identify and/or quantify degranulating neutrophils and/or NETs based on morphological features. For example, a data analysis module including a trained artificial intelligence architecture can be loaded onto an automated imaging system or other computing device. The data analysis module can be used to automatically review images of a biological sample to identify, sort, and/or count, if present, the number of NETs in the biological sample. The artificial intelligence architecture can include an artificial neural network system utilizing convolutional neural networks, pooling, and/or deep learning. Thus, in some embodiments, a computing device can determine the presence or absence of NETs in a biological sample using a trained depthwise separable convolutional neural network (DS-CNN). Moreover, in some embodiments, the computing device can count the number of NETs present in a biological sample using the trained DS-CNN.

As one skilled in the art will understand from the following description, the present technology can be implemented in a variety of ways, including, for example, as processes, methods, systems, devices, instructions for computer-readable mediums, computer-readable mediums, and the like. Accordingly, one skilled in the art will recognize the present technology has numerous applications and is not limited to those explicitly discussed herein.

The terminology used in the description presented below is intended to be interpreted in its broadest reasonable manner, even though it is being used in conjunction with a detailed description of certain specific embodiments of the present technology. Certain terms may even be emphasized below; however, any terminology intended to be interpreted in any restricted manner will be overtly and specifically defined as such in this Detailed Description section. Additionally, the present technology can include other embodiments that are within the scope of the claims but are not described in detail with respect to FIGS. 1A-18B.

Reference throughout this specification to "one embodiment" or "an embodiment" means that a particular feature, structure or characteristic described in connection with the embodiment is included in at least one embodiment of the present technology. Thus, the appearances of the phrases "in one embodiment" or "in an embodiment" in various places throughout this specification are not necessarily all referring to the same embodiment, nor necessarily to different embodiments. Furthermore, the particular features or characteristics may be combined in any suitable manner in one or more embodiments.

Reference throughout this specification to relative terms such as, for example, "approximately" and "about" are used herein to mean the stated value plus or minus 10%, unless the context clearly dictates otherwise.

The headings provided herein are for convenience only and do not affect the scope or meaning of the claimed present technology.

A. Neutrophil Extracellular Traps (NETs) and Infections

NETs are extracellular decondensed chromatin networks that can include granule proteins, DNA, histones, and other matter. NETs are generated by neutrophils to engulf and kill pathogens, and may form during infection, inflammation, and/or thrombosis. More specifically, when a neutrophil detects a pathogen, granule proteins, DNA, and/or histones may combine within the neutrophil. The neutrophil can then eject the combined granule proteins, DNA, and/or histones to form NETs (e.g., the nuclear and granular membranes disintegrate, permitting intracellular material to be "ejected" from the cell). The NETs can then capture, bind, engulf, and/or kill the pathogen in a process called netosis. Because they originate from neutrophils and because they play a role in combating infection, NETs are commonly found extravascularly in inflamed or infected tissues. However, NETs can also be present in a patient's blood when a patient is infected with certain pathological conditions. For example, an increased number of NETs (extravascularly and/or within the patient's blood) is correlated with various pathological conditions, including sepsis, bacterial infection (e.g., *streptococcus* sp., *Hemophilus influenzae, Klebsiella pneumoniae, Listeria monocytogenes, Mycobacterium tuberculosis, Shigella flexneri, Yersinia, Staphylococcus aureus*), fungal infections (e.g., *aspergillus* sp., *Candida albicans*), viral infections (e.g., HIV), and non-infections (e.g., thrombosis, sickle cell disease, autoimmune disease, solid organ transplants, liver disease, diabetes, cancer, and other malignancies). This finding suggests that the presence of, and/or the increase in the number of, NETs signifies the patient may be in an inflammatory or otherwise "sickened" state.

In particular, an increased number of NETs in blood is associated with infections (e.g., bacterial, fungal, viral). If not treated early, or if treated poorly, some infections may lead sepsis. Sepsis is a systemic inflammatory response to an infection. The systemic inflammatory response can cause multi-organ dysfunction, multi-organ failure, shock, and death. While treatments exist to reduce the severity of sepsis (e.g., to reduce the likelihood of a patient dying from sepsis), mortality rates nevertheless remain high. This is at least in part because there are no definite diagnosis criteria for identifying sepsis. Instead, clinicians rely upon a combination of blood tests, imaging tests, and symptom review to determine whether a patient has sepsis. As a result of the complexity of this analysis, both the diagnosis of sepsis and the treatment of sepsis are often delayed. Due to the severity of sepsis, even a slight delay in treatment can greatly reduce a patient's likelihood of survival. Accordingly, delayed diagnosis of sepsis can be directly tied to increased mortality. As will be described in greater detail below, the present technology provides an approach that can quickly and accurately identify infections that may lead to sepsis and/or quickly and accurately identify the early stages of sepsis itself by identifying, characterizing, and/or enumerating NETs in blood samples. Thus, without being bound by theory, one advantage of the present technology is providing a diagnosis technique that can facilitate early intervention/treatment and to decrease the mortality rate of infections and/or sepsis.

The formation of NETs during infection is robust and may even contribute to sepsis progression. For example, it has been shown that neutrophils interact with and adhere to platelets during infection. More specifically, activated platelets express P-selectin, which is an adhesion molecule released from the α-granules during activation. Neutrophils recognize and bind P-selectin via the P-selection glycoprotein ligand-1 (PSGL-1) receptor. Platelet-neutrophil interactions can induce hyperactivation of neutrophils, thereby facilitating a physiological response that results in increased NET formation. Increased NET formation can activate thrombin and cause increased inflammation, which plays a central role in disseminated intravascular coagulopathy, a severe complication in sepsis. In particular, platelet-neutrophil complexes and NETs have been shown to aggregate in the microvasculature of the lungs and liver during infection, which may contribute to the organ failure seen in sepsis. Therefore, while NETs can play a role in capturing circulating pathogens, NETs may also promote platelet coagulation and organ damage common to sepsis.

At the least, as described in detail below in Examples 3 and 4, NET formation and infections that can lead to sepsis are strongly correlated, and NETs can often begin to form even before clinical symptoms of sepsis appear. Accordingly, NETs can function as a biomarker useful in identifying patients who may develop an infection and/or sepsis even before any symptoms appear. By identifying NETs as an indicator of infection or sepsis, patients can begin treatment earlier, thereby increasing their likelihood of surviving the infection or sepsis. However, it remains difficult to detect, characterize, and enumerate NETs using conventional technologies. The present technology therefore provides systems, devices, and methods that can be used to more easily identify NETs in patients, and thus is expected to be useful in aiding in the diagnosis of various infections and/or sepsis.

B. Identifying NETs in Blood

As provided above, the present technology provides systems, device, and methods for identifying NETs in a biological sample. In some embodiments, for example, the present technology identifies, characterizes, and/or enumerates NETs in a blood sample, such as a blood smear (e.g., a peripheral blood smear), a CBC scattergram, or the like. In some embodiments, the present technology can identify NETs based on morphological features. In some embodiments, the present technology can identify NETs solely based on morphological features. Without being bound by theory, identifying NETs based on morphological features may decrease the time required to identify and/or enumerate NETs, as compared to other techniques, thus aiding in fast diagnosis times.

The present technology provides systems and methods for identifying NETs in common blood samples. Blood is routinely drawn from patients during hospital stays, in-patient visits, out-patient visits, clinic visits, and the like to run a variety of diagnostic tests. CBCs, for example, are a set of common lab tests performed using a patient's blood that give information about the cells in a person's blood. A CBC will typically report the amounts of white blood cells, red blood cells, and platelets, the concentration of hemoglobin in the blood, and the hematocrit. In some embodiments, automated or semi-automated imaging systems and/or automated or semi-automated hematology analyzers (herein referred to collectively as "automated imaging systems") are used perform various aspects of the CBC (e.g., automatically image, count, and/or sort various blood cell types). Exemplary automated imaging systems include the CellaVision®, Nextslide Digital Review Network, Vision Hema Ultimate, and the like. In some embodiments, automated imaging systems can automatically locate and image cells in a provided biological sample. Following imaging, the systems can automatically analyze and pre-sort the imaged cells into various categories for digitized clinician review and verification. In some embodiments, cells may be stained or otherwise treated before being loaded into the automated imaging system for analysis. For example, in some embodiments, a user may prepare a blood smear (e.g., a peripheral blood smear), and then load the blood smear sample into the automated imaging system for further review/quantification.

As noted above, biological samples such as blood/blood smears are often stained before being loaded into an automated imaging system, or the automated imaging system stains the received samples before imaging and analyzing the samples. For example, Wright Giemsa stains can be used to stain peripheral blood smears and prepare samples for morphological analysis. Wright Giemsa stains can comprise oxidized methylene blue, azure B, and eosin Y dyes. The eyosin Y dye stains the cytoplasm of cells an orange to pink color, while the methylene blue and azure B dyers stain the nucleus varying shades of blue to purple. Accordingly, Wright Giemsa stains can be used to perform differential white blood cell counts and can be incorporated into automated imaging systems, such as those discussed herein.

Additionally or alternatively, other staining technologies known in the art can be used in conjunction with automated imaging systems.

Certain cells are not readily recognized by existing automated imaging systems. Cells not recognized by existing imaging systems may be labeled as "other", "unidentified", or "smudge" cells (collectively referred to herein as "smudge cells"). Traditionally, smudge cells have been thought to include degenerating cells (e.g., degenerating lymphocytes commonly referred to as "basket" cells) and/or remnants of white blood cells that are no longer viable. As a result of this assumption, high levels of smudge cells are typically associated with chronic lymphocytic leukemia (CLL). Accordingly, automated imaging systems and clinicians have traditionally ignored and/or not reported smudge cells when reviewing CBCs, unless the patient has CLL or is at risk for CLL. However, as will be described in greater detail below, the present technology recognizes that smudge cells can also contain NETs. In particular, smudge cells found in blood samples frequently include degranulating neutrophils and NETs.

Figure 1E:
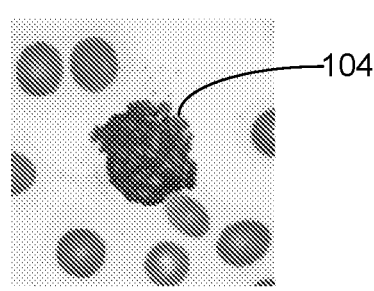
Figure 1F:
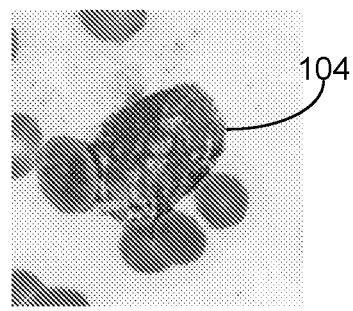

FIGS. 1A-1F are a series of images of Wright Giemsa stained cells 104 that were identified as smudge cells by an automated imaging system. In particular, FIGS. 1A-1D illustrate the stained cells 102 as degenerating lymphocytes, and FIGS. 1E and 1F illustrate the stained cells 104 as degenerating lymphocytes that have progressed to basket cells. As described above, the stained cells 102 and 104 have been previously identified as smudge cells in automated imaging systems.

Figure 2A:
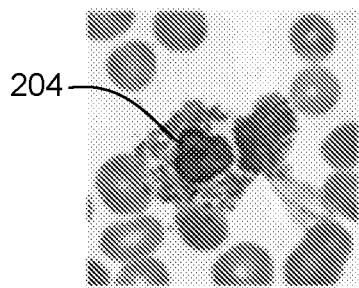
FIGS. 2A-2D are images of Wright Giemsa stained biological samples containing degranulating neutrophils and neutrophil extracellular traps (NETs) in accordance with embodiments of the present technology.
Figure 2B:
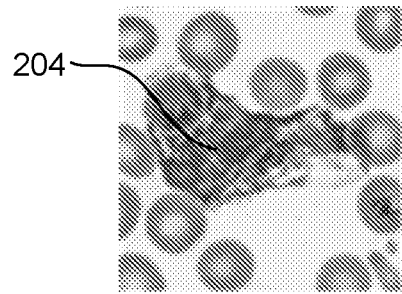
Figure 2C:
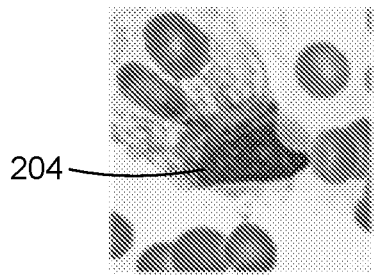
Figure 2D:
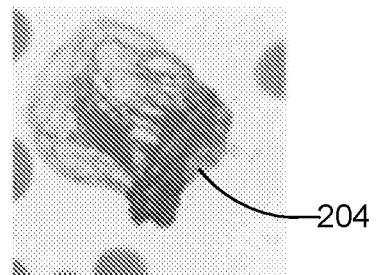

FIGS. 2A-2D are series of images of Wright Giemsa stained cells 204 that were also identified as smudge cells by an automated imaging system. However, the cells shown in FIGS. 2A-2D are taken from a different biological sample than the cells shown in FIGS. 1A-1F. Unlike in FIGS. 1A-1D, several of the stained cells 204 shown in FIGS. 2A-2D include certain morphological features consistent with those of NETs at various stages of netosis. In particular, the stained cells 204 in FIGS. 2A-2D appear as cell remnants without a discernable plasma membrane, with decondensed and congested nuclei with no intact cytoplasm, and/or with dispersed granules and polarized chromatin projections that resemble spider webs. The relative degree of these morphological characteristics depends on the maturity of the NETs. For example, FIG. 2A illustrates an early stage of netosis where relatively small amounts of the DNA and granule proteins have been ejected from the neutrophil. In contrast, FIG. 2D illustrates a more mature NET at a later stage of netosis, where relatively large amounts of DNA, granule proteins, and/or histones have been ejected from the neutrophil. As will be discussed below with respect to FIGS. 3A-5B, the cells 204 have been confirmed as NETs through non-morphological analysis. Thus, the present technology provides evidence that NETs can be identified in blood samples based on one or more morphological features of cells.

Figure 3A:
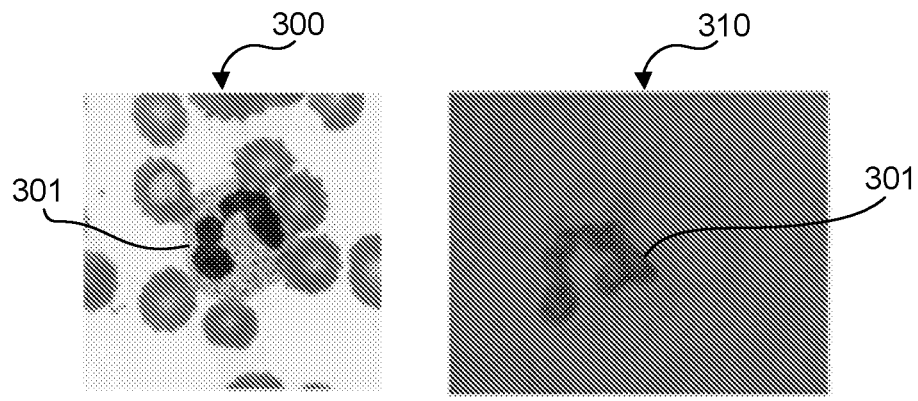
FIG. 3A includes a series of images of intact neutrophils in a biological sample prepared using Wright Giemsa staining and neutrophil elastase staining in accordance with embodiments of the present technology.
Figure 3B:
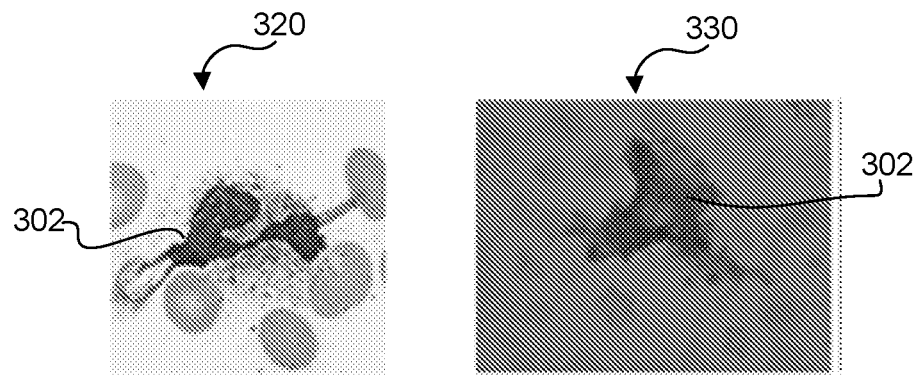
FIG. 3B includes a series of images of degranulating neutrophils in a biological sample prepared using Wright Giemsa staining and neutrophil elastase staining in accordance with embodiments of the present technology.
Figure 3C:
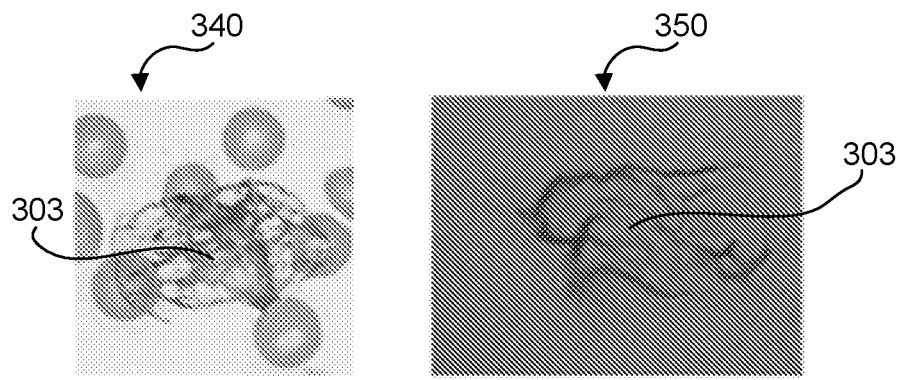
FIG. 3C includes a series of images of mature NETs in a biological sample prepared using Wright Giemsa staining and neutrophil elastase staining in accordance with embodiments of the present technology.

FIGS. 3A-3C illustrate the presence of neutrophils and NETs in samples classified as smudge cells using neutrophil elastase staining. Neutrophil elastase is highly expressed in NETs and binds the chromatic and histone proteins ejected from the neutrophil during NET formation. Thus, to confirm the presence of NETs in the smudge cells, the smudge cells can be stained with anti-neutrophil elastase antibody. FIG. 3A includes a first image 300 and a second image 310 prepared using Wright Giemsa staining and neutrophil elastase staining, respectively. Images 300 and 310 are of the same biological sample (but not necessarily the same cell) and illustrate an intact neutrophil 301. FIG. 3B includes a first image 320 and a second image 330 prepared using Wright Giemsa staining and neutrophil elastase staining, respectively. Images 320 and 330 are of the same biological sample (but not necessarily the same cell) and illustrate a degranulating neutrophil 302 in the process of ejecting intracellular matter such as DNA and/or proteins. FIG. 3C includes a first image 340 and a second image 350 prepared using Wright Giemsa staining and neutrophil elastase staining, respectively. Images 340 and 350 are of the same biological sample (but not necessarily the same cell) and illustrate a mature NET 303.

Figure 4A:
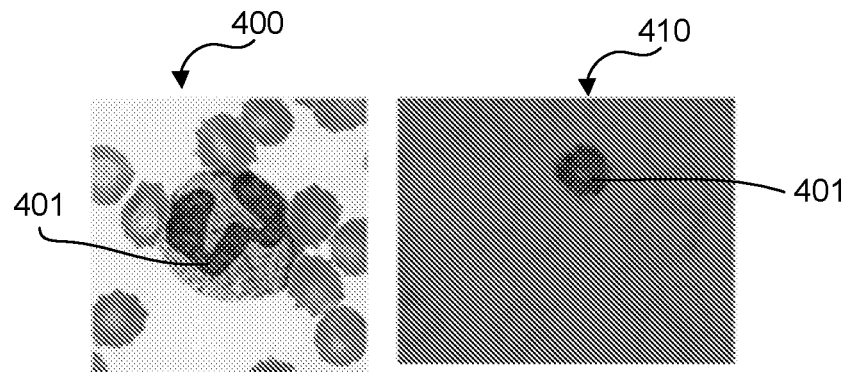
FIG. 4A includes a series of images of intact neutrophils in a biological sample prepared using Wright Giemsa staining and myeoloperoxidase (MPO) staining in accordance with embodiments of the present technology.
Figure 4B:
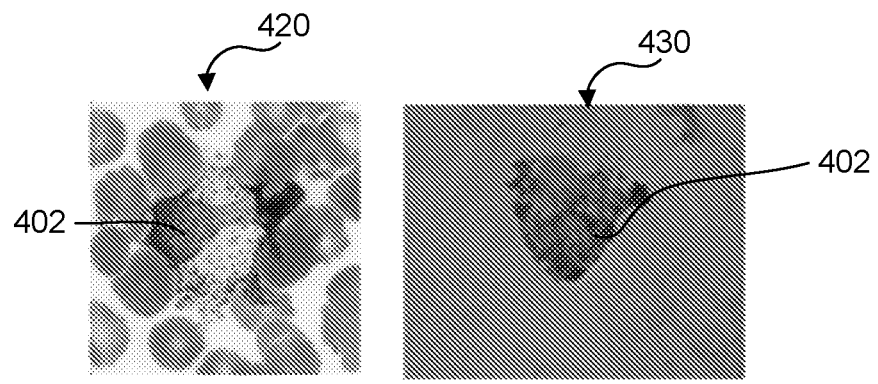
FIG. 4B includes a series of images of degranulating neutrophils in a biological sample prepared using Wright Giemsa staining and MPO staining in accordance with embodiments of the present technology.
Figure 4C:
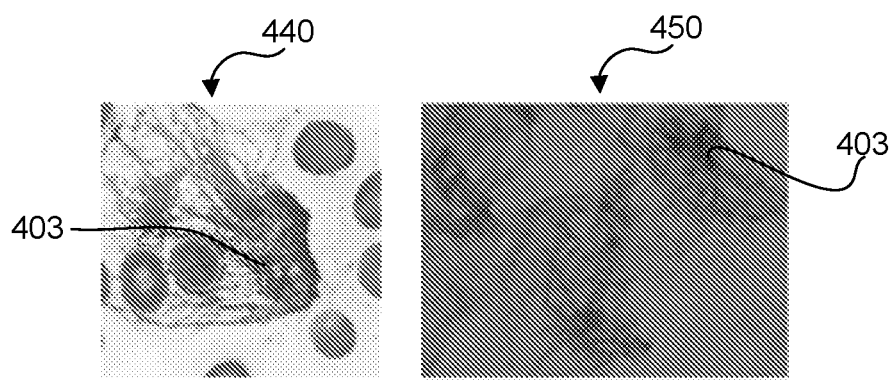
FIG. 4C includes a series of images of mature NETs in a biological sample prepared using Wright Giemsa staining and MPO staining in accordance with embodiments of the present technology.

FIGS. 4A-4C illustrate the presence of neutrophils and NETs in samples classified as smudge cells using myeoloperoxidase (MPO) staining. MPO is a protein that is often highly expressed in neutrophils and/or NETs. Accordingly, staining with MPO activity can identify both degranulating neutrophils that are becoming NETs and mature NETs. FIG. 4A includes a first image 400 and a second image 410 prepared using Wright Giemsa staining and MPO staining, respectively. Images 400 and 410 are of the same biological sample (but not necessarily the same cell) and illustrate an intact neutrophil 401. FIG. 4B includes a first image 420 and a second image 430 prepared using Wright Giemsa staining and MPO staining, respectively. Images 420 and 430 are of the same biological sample (but not necessarily the same cell) and illustrate a degranulating NET 402 in the process of ejecting intracellular matter such as DNA and/or proteins. FIG. 4C includes a first image 440 and a second image 450 prepared using Wright Giemsa staining and MPO staining, respectively. Images 440 and 450 are of the same biological sample (but not necessarily the same cell) and illustrate a mature NET 403.

Figure 5A:
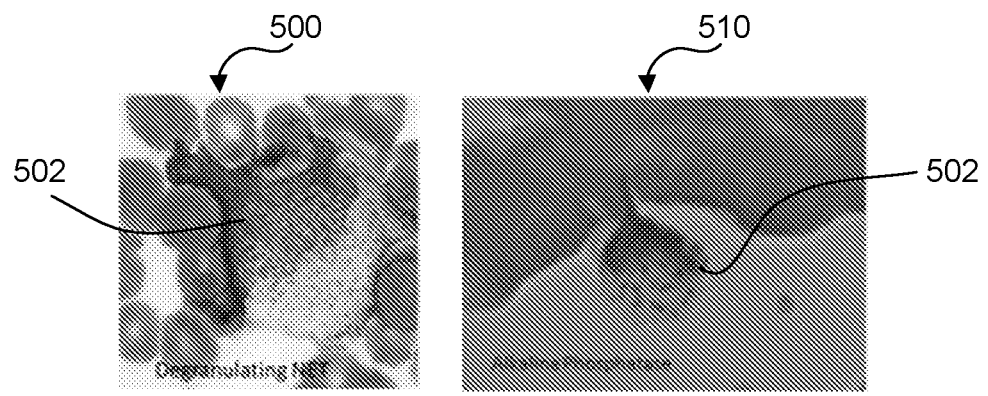
FIG. 5A includes a series images of degranulating neutrophils in a biological sample prepared using Wright Giemsa staining and Leukocyte alkaline phosphatase (LAP) staining in accordance with embodiments of the present technology.
Figure 5B:
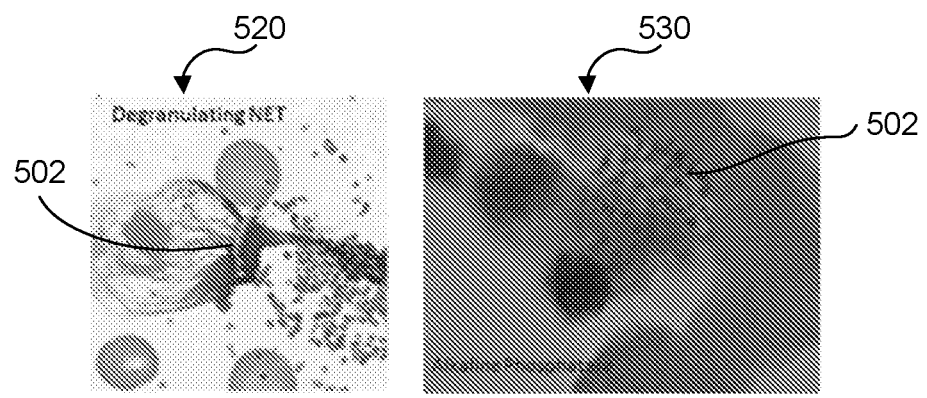
FIG. 5B includes a series of images of degranulating neutrophils in a biological sample prepared using Wright Giemsa staining and LAP staining in accordance with embodiments of the present technology.

FIGS. 5A-5B illustrate the presence of neutrophils and NETs in samples classified as smudge cells using anti-leukocyte alkaline phosphatase staining. Leukocyte alkaline phosphatase (LAP) is another protein highly expressed by neutrophils and/or NETs. LAP expression can also be associated with sepsis. FIG. 5A includes a first image 500 and a second image 510 prepared using Wright Giemsa staining and LAP staining, respectively. Images 500 and 510 are of the same biological sample (but not necessarily the same cell) and illustrate a degranulating neutrophil 502 in the process of ejecting intracellular matter such as DNA and/or proteins. FIG. 5B includes a first image 520 and a second image 530 prepared using Wright Giemsa staining and LAP staining, respectively. Images 520 and 530 are of the same biological sample (but not necessarily the same cell) and illustrate a degranulating neutrophil 502 in the process of ejecting intracellular matter such as DNA and/or proteins.

As FIGS. 3A-5B illustrate, neutrophils, degranulating neutrophils, and NETs can be identified in blood (e.g., in peripheral blood smears). In particular, neutrophils, degranulating neutrophils, and NETs can be identified in blood samples classified as smudge cells by automated imaging systems. This is in contrast to conventional teachings, in which smudge cells were thought to only include degenerating lymphocytes or other remnants of white blood cells that are no longer viable. The present disclosure, however, shows that neutrophils, degranulating neutrophils, and NETs can also be included in cells that are classified as smudge cells by automated imaging systems. Notably, these neutrophils, degranulating neutrophils, and NETs can be detected and distinguished from other types of smudge cells based on their morphology. As will be described in greater detail below, NETs can therefore be used as a biomarker in predicting development of certain conditions, such as infections and/or sepsis.

Certain embodiments of the present technology provide methods for identifying NETs in peripheral blood smears. For example, select methods can include obtaining a biological sample from a human patient (e.g., through venipuncture, finger-prick, or other suitable techniques known in the art). The biological sample can be stained and imaged through manual processes known in the art and/or via automated imaging systems to generate a plurality of images, with each image corresponding to one or more cells in the biological sample. In some embodiments, for example, the biological sample is prepared with a Wright Giemsa stain or another suitable stain. In some embodiments, the plurality of images can be pre-sorted by an automated imaging system, while in other embodiments, the plurality of images are not pre-sorted by an automated imaging system. If pre-sorted by an automated imaging system, the images classified as smudge cells can be analyzed by a clinician (e.g., a pathologist), and, based on the morphology of the imaged sample, the clinician can determine whether the biological sample contains NETs. If the number of NETs identified in a given sample from a single patient exceeds a predetermined threshold, the clinician can diagnose the patient with a pathological condition such as sepsis. If the images are not pre-sorted by an automated imaging system, a clinician can nonetheless analyze the images for morphological features indicative of NETs and use the information to aid in a diagnosis of sepsis or other pathological condition. While the above methods describe analyzing images of biological samples, one skilled in the art will appreciate that a clinician could also directly view the stained biological sample through a microscope to visualize NETs in peripheral blood smears and aid in the diagnosis of sepsis or other pathological conditions.

C. Artificial Intelligence Architectures to Identify NETs

In some embodiments, the present technology uses artificial intelligence to automatically identify and/or quantify degranulating neutrophils and/or NETs in a peripheral blood smears based on morphological features. For example, a software module including a trained artificial intelligence architecture can be loaded onto an automated imaging system or other computing device. The software module can be used to automatically review images of a biological sample to identify, sort, and/or count, if present, the number of NETs in the biological sample. The artificial intelligence architecture can include an artificial neural network system utilizing convolutional neural networks, pooling, and/or deep learning. Thus, in some embodiments, a computing device can determine the presence or absence of NETs in a biological sample using a software module having a trained convolutional neural network (CNN). Moreover, in some embodiments, the computing device can count the number of NETs present in a biological sample using the software module.

Convolution neural networks (CNNs) are computational models that enable a machine to learn about and/or classify visual information. For example, CNNs can identify and classify objects such as faces. CNNs can be employed in medical imaging in areas such as retinopathy screening, bone disease prediction, and age assessment. Moreover, CNNs can be used in histological image analysis. For example, CNN based histological microscopic image analysis can be used in diagnosing certain cancers (e.g., breast cancer). There are several drawbacks to using CNNs in medical analysis. For example, use of CNNs requires large data samples, high computational power, and long learning periods before being able to accurately identify and classify images. For example, training a standard CNN to identify and classify a new image (e.g., identifying a stained cell in a histological image) in some cases involves thousands of high-resolution images, thousands of graphical processing units (GPUs), and hours or even days to train. Accordingly, while standard CNNs offer some benefits in medical imaging and diagnosis, several drawbacks remain.

The present technology relies on depthwise separable CNNs (DS-CNNs) to classify imaged cells. Unlike traditional CNNs, DS-CNNs can classify cytological images with high accuracy despite limited training sample size, limited computation power, and limited time. Thus, in some embodiments, the present technology uses DS-CNN architectures to classify NETs versus degenerative lymphocytes. As will be described in greater detail below, the present technology adds DS-CNN architectures to pre-existing automated imaging systems (e.g., CellaVision, Sysmex, etc.) to allow the automated imaging systems to classify certain images as including NETs. In some embodiments, the present technology adds DS-CNN architectures to another computing device (e.g., a mobile phone) and uses the DS-CNN architectures to classify histological images through a mobile phone camera in real time.

DS-CNNs rely on a unique architecture to make them computationally efficient and fast. A standard convolutional layer takes as input a $D_F \times D_F \times M$ feature map F (i.e., an input feature map F) and produces a $D_G \times D_G \times N$ feature map G (i.e., an output feature map G) where $D_F$ is the spatial width and height of a square input feature map, M is the number of input channels (input depth), $D_G$ is the spatial width and height of a square output feature map, and N is the number of output channel (output depth). The standard convolutional layer is parameterized by convolution kernel K of size $D_K \times D_K \times M \times N$ where $D_K$ is the spatial dimension of the kernel assumed to be square and M is the number of input channels and N is the number of output channels as defined previously.

Figure 6A:
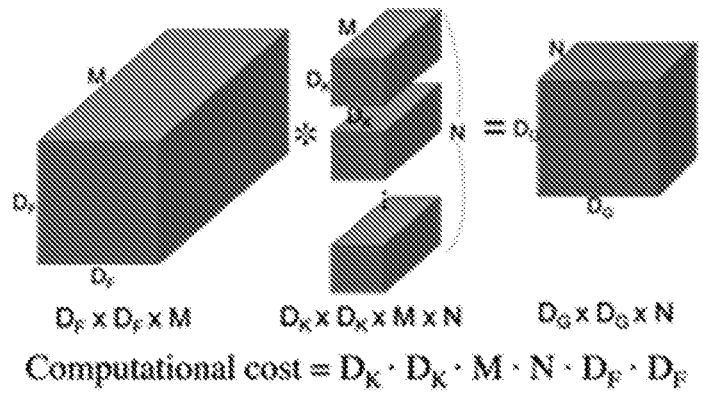
FIG. 6A is a schematic illustration of a standard convolutional neural network architecture configured in accordance with embodiments of the present technology.
Figure 6B:
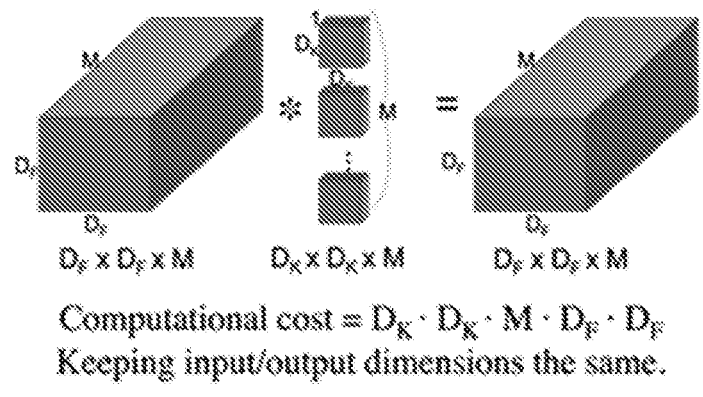
FIG. 6B is a schematic illustration of a depthwise convolution of a depthwise separable convolutional neural network architecture configured in accordance with embodiments of the present technology.

As illustrated in FIG. 6A, a standard CNN filters and combines input into a new set of outputs in one layer. Thus, the computation cost of standard convolution is:

$$D_K \cdot D_K \cdot M \cdot N \cdot D_F \cdot D_F \quad (1)$$

Figure 6C:
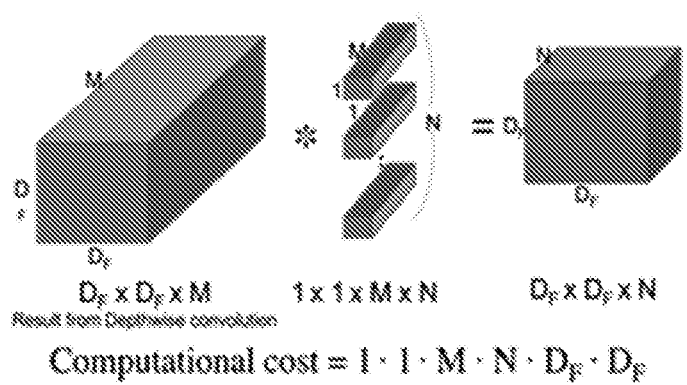
FIG. 6C is a schematic illustration of a pointwise convolution of a depthwise separable convolutional neural network architecture configured in accordance with embodiments of the present technology.

In DS-CNN, however, this cost is split into two layers: depthwise convolution (illustrated in FIG. 6B) and pointwise convolution (illustrated in FIG. 6C). The depthwise convolution is computed first from the input image. It applies single filter per each input channel. For example, $m^{th}$ filter in K is applied to the $m^{th}$ channel in F to produce the $m^{th}$ channel of the output feature map G. However, depthwise convolution filters input channels but does not combine them to create new features. Therefore, 1×1 pointwise convolution is applied to the result of depthwise convolution in order to generate new features. The computational cost of depthwise convolution is:

$$DK \cdot DK \cdot M \cdot DF \cdot DF \quad (2)$$

The computational cost of pointwise (1×1) convolution is:

$$1 \cdot 1 \cdot M \cdot N \cdot DF \cdot DF \quad (3)$$

Therefore, from (2) and (3), depthwise separable convolution has a computational cost of:

$$(DK \cdot DK \cdot M \cdot DF \cdot DF) + (1 \cdot 1 \cdot M \cdot N \cdot DF \cdot DF) \quad (4)$$

The reduction of computation from (1) to (4) can thus be calculated as:

$$\frac{(D_K \cdot D_K \cdot M \cdot D_F \cdot D_F) + (1 \cdot 1 \cdot M \cdot N \cdot D_F \cdot D_F)}{D_K \cdot D_K \cdot M \cdot N \cdot D_F \cdot D_F} = \frac{1}{N} + \frac{1}{D_K^2} \simeq \frac{1}{9} \quad (5)$$

Some embodiments of the present technology use a full convolutional first layer, with each subsequent layer having 3×3 depthwise separable convolutions to reduce computational requirements. For example, counting depthwise and pointwise convolution as separate layers, embodiments of the present technology can include architectures with 28 layers. As one skilled in the art will appreciate, however, other embodiments include more or fewer layers, and each layer can have more or fewer depthwise separable convolutions. For example, in some embodiments, the present technology includes architectures having between 3 layers and 40 layers, or between 10 layers and 40 layers, or between 15 layers and 40 layers, or between 20 layers and 40 layers. The present technology can also include architectures with fewer than 3 layers or greater than 40 layers. In some embodiments, the layers include one or more feature filters configured to extract one or more features from a region of units using a convolution, apply an additive bias, and/or apply a sigmoid function. In some embodiments, the one or more features comprise one or more of the following: (1) one or more local features, (2) one or more global features, (3) one or more edges, (4) one or more colors, (5) one or more intensity level, (6) one or more spatial features, and (7) one or more shape features.

Without being bound by theory, based on formulas (2)-(4), it is expected that the use of depthwise separable convolutions leads to approximately 8 to 9 times less computation than standard convolutions, with only a slight reduction in accuracy. All layers can be followed by batchnorm and ReLU nonlinearity with the exception of the final fully connected layer which can have no nonlinearity and can feed into a softmax layer for classification.

In some embodiments, the DS-CNN architectures provided herein can include a width multiplier $\alpha(0<\alpha\leq 1)$. The width multiplier $\alpha$ can be used to uniformly thin a neural network at each layer. For example, for a given layer and width multiplier $\alpha$, the number of input channels M become $\alpha$M, and the number of output channels N becomes $\alpha$N. In some embodiments of the present technology, $\alpha=1$, although other embodiments use values ranging from 0 to less than 1. As one skilled in the art will appreciate, a number of variations on inputs and parameters could be made to the described architecture while remaining within the scope of the present technology. For example, parameters such as input image resolution, training batch size, validation batch size, and learning rates can be manipulated.

As noted above, some embodiments of the present technology use depthwise separable CNNs (DS-CNNs) to identify NETs. For example, in some embodiments, the DS-CNN architecture classifies NETs versus degenerative lymphocytes (DL) among cells classified as "smudge cells" by an automated imaging system. In some embodiments, DS-CNNs are used to identify patients having sepsis, infection, inflammation, and/or thrombosis. In some embodiments, the DS-CNN can identify patients having sepsis, infection, inflammation, and/or thrombosis before the conditions cause symptoms in the patient. As a result, the patient can start treatment sooner, increasing the likelihood of patient survival.

The DS-CNN architectures described herein can be provided in a number of applications. For example, the DS-CNN architectures may be applied to current automated imaging systems (e.g., CellaVision, Sysmex, etc.). Accordingly, in some embodiments, the DS-CNN architectures are included in a software update to existing automated imaging systems to enable the automated imaging systems to identify and classify NETs as part of routinely performed CBCs. In some embodiments, the DS-CNN architectures are integrated into devices designed to identify NETs as a way of predicting the onset of certain conditions, such as sepsis. In some embodiments, DS-CNN architectures are downloaded onto mobile devices (e.g., cell phones, tablet computers, etc.). Once downloaded onto a mobile device, the DS-CNN architectures can be used to classify histological images through a camera on the device in real time. In some embodiments, the mobile device camera captures images of a stained biological sample or an image of the stained biological sample. The application providing a platform for the DS-CNN architectures then analyzes and/or classifies the captured image. In some embodiments, the mobile device camera is simply turned on (when in the application) and directed at the stained image or sample. In such embodiments, the DS-CNN architectures analyze and/or classify the stained image or sample without the mobile phone needing to capture and store an image of the stained image or sample. Applying the DS-CNN architectures on a mobile device can be useful in scenarios where there are no pathologists or high-end computers readily available for histological image analysis.

The present technology further provides methods for identifying NETs in a peripheral blood smear using artificial intelligence architectures and networks as described herein. For example, a biological sample containing white blood cells can be stained and imaged via automated imaging systems to generate a plurality of images, with each image corresponding to one or more cells in the biological sample. An automated imaging system may pre-classify certain cells as "smudge cells." Using the DS-CNN architectures provided herein, the automated imaging system can then classify smudge cells as either NETs, degenerating lymphocytes, or neither. The automated imaging systems can then provide digitized images of the pre-sorted cells for clinician review and analysis. In some embodiments, the automated imaging system also provides a confidence score for each of the images indicating the likelihood that an image contains a NET. In some embodiments, the automated imaging system also indicates the total number of NETs and/or ratio of NETs to other white blood cells in the biological sample. If the total number and/or ratio exceeds a predetermined threshold, the system can indicate that a diagnosis of sepsis is likely. In some embodiments, the methods further include a training step. For example, the DS-CNN architecture can be trained on previously classified images to increase the sensitivity and accuracy of the program.

Figure 7A:
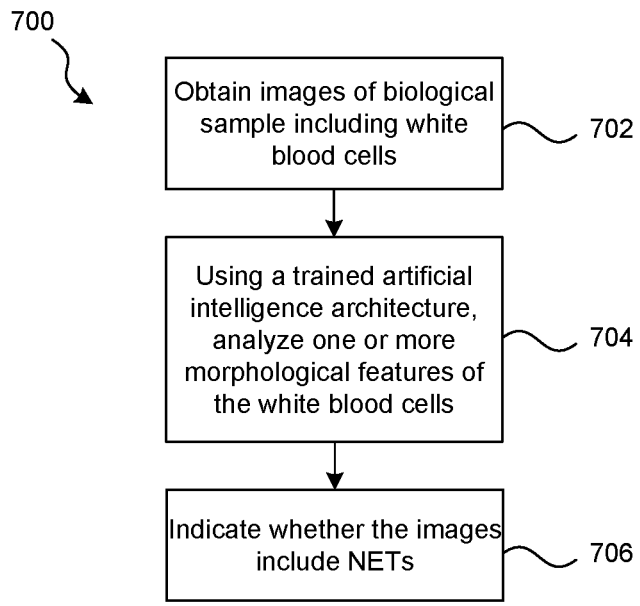
FIGS. 7A and 7B are flowcharts of methods for identifying NETs in blood samples in accordance with embodiments of the present technology.

FIG. 7A illustrates a computer-implement method 700 for identifying neutrophil extracellular traps in a blood sample using a computing system in accordance with embodiments of the present technology. The method 700 includes obtaining, in step 702, images of a biological sample including white blood cells. In some embodiments, the images can be images of a peripheral blood smear. The method 700 can continue in step 704 by analyzing one or more morphological features of the white blood cells using a trained artificial intelligence architecture, such as a depthwise separable convolution neural network as previously described above. In step 706, the computing system can indicate (e.g., via a display) whether the patient's blood includes NETs. The computing system can also indicate other information, such as the total number of (or an estimated total number of) NETs identified in the images and/or a ratio of (or an estimated ratio of) NETs to other white blood cells. The computing system may also provide a confidence score for each of the images indicating the likelihood that an image contains a NET. The computing system may also sort the imaged cells into categories for clinician review.

Figure 7B:
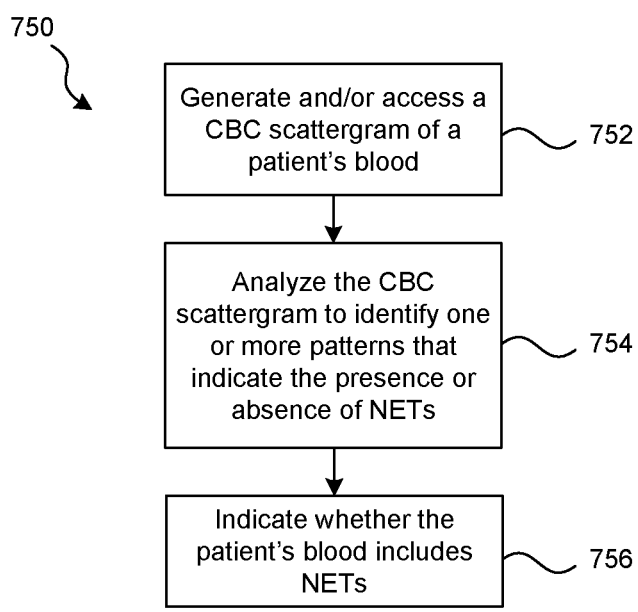

Although the artificial intelligence systems and architectures are primarily described herein as identifying NETs in peripheral blood smears based on morphology, one skilled in the art will appreciate that the artificial intelligence systems can also be adapted to identify, enumerate, and/or characterize NETs based on CBC scattergrams and/or flow cytometry results. For example, in some embodiments, an artificial intelligence system can be trained using a plurality of CBC scattergrams to identify NETs, which, as described below in Example 2, occupy a specific, previously unidentified area on the CBC scattergram. The trained artificial intelligence system can then be used to analyze a CBC scattergram plot to identify and enumerate, if present, a relative level of NETs in the biological sample. FIG. 7B, for example, illustrates a method 750 (e.g., a computer-implemented method) for identifying NETs using a CBC scattergram in accordance with embodiments of the present technology. In step 752, a computing system or device can generate and/or access a CBC scattergram. In step 754, the computing system can analyze, via a data analysis module including an artificial intelligence architecture, the CBC scattergram to identify one or more patterns in the CBC scattergram that indicate the presence or absence of NETs. In some embodiments, analyzing the CBC scattergram includes analyzing the fluorescence within a predetermined area on the CBC scattergram that is associated with neutrophil extracellular traps. In step 756, the computing system can indicate (e.g., via a display) whether the patient's blood includes NETs. The computing system can also indicate other information, such as the total number of (or an estimated total number of) NETs identified in the CBC scattergram and/or a ratio of (or an estimated ratio of) NETs to other white blood cells.

Figure 8:
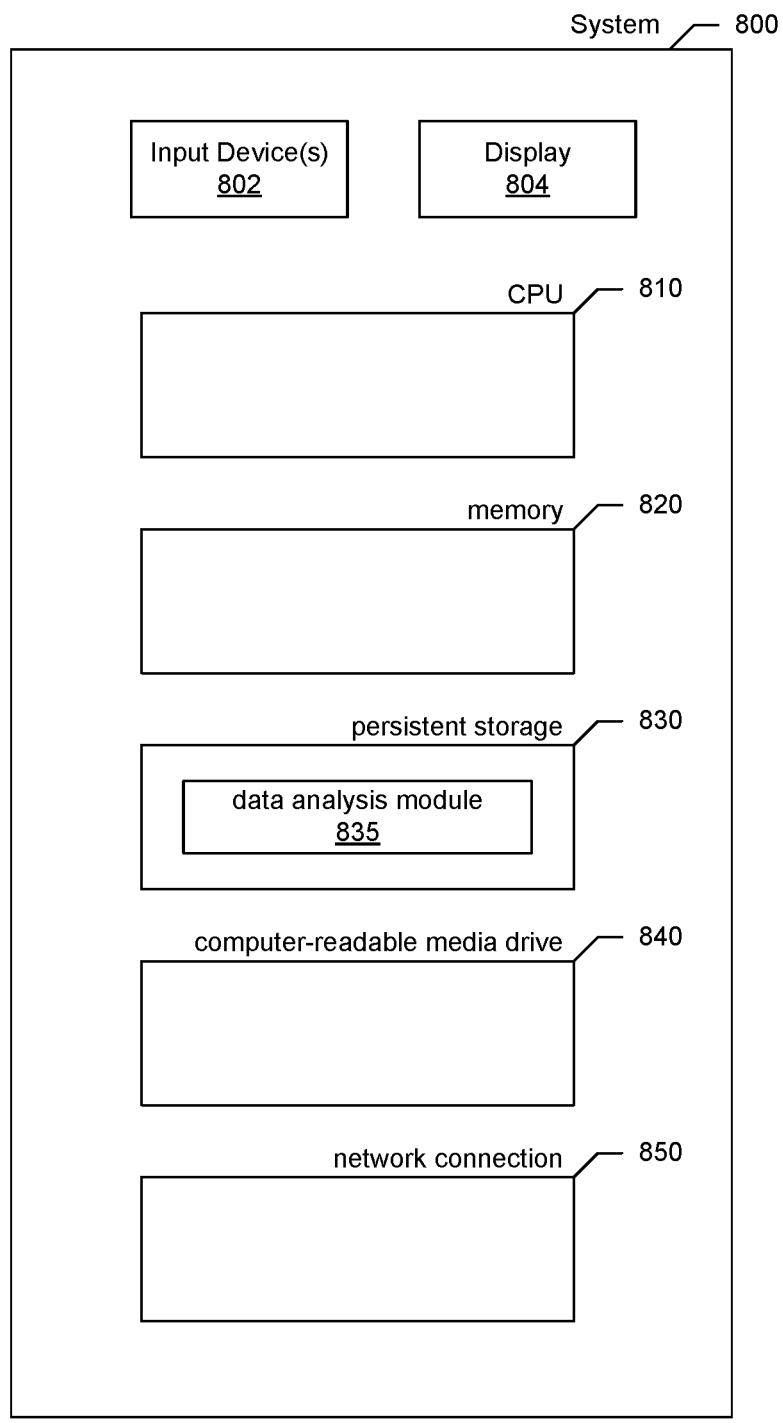
FIG. 8 is a schematic illustration of a computing device configured in accordance with select embodiments of the present technology.

FIG. 8 is a block diagram showing some of the components typically incorporated in computing systems configured in accordance with select embodiments of the present technology. For example, in some embodiments the system 800 can be an automated imaging system, as previously described herein. The system 800 can also be another suitable computing system, incorporating various computing devices such as a smart phone, mobile device, desktop computer, laptop computer, tablet, or other devices known in the art. In various embodiments, the system 800 can include one or more of each of the following: a central processing unit ("CPU") 810 having one or more processors for executing computer programs, such as the artificial intelligence architectures and software modules described herein; a computer memory 820 for storing programs and data while they are being used, including the facility and associated data, an operating system including a kernel, and device drivers; a persistent storage device 830, such as a hard drive or flash drive for persistently storing programs and data (e.g., one or more data analysis modules 835, including the trained artificial intelligence architectures described herein); a computer-readable media drive 840, such as a floppy, CD-ROM, DVD drive, USB port, or USB-C port for reading programs and data stored on a separate computer-readable medium; and a network connection 850 for connecting the system 800 to other computing systems, a network server, and/or the "cloud", to send and/or receive data, such as via the Internet or another network and its networking hardware, such as switches, routers, repeaters, electrical cables and optical fibers, light emitters and receivers, radio transmitters and receivers, and the like. For example, via the network connection 850, the system 800 can retrieve data from a remote data storage location (e.g., a cloud data storage location, a remote server, etc.). In some embodiments, the system 800 includes one or more input devices 802 that provide input to the CPU 810, such as to notify the CPU 810 of one or more actions or desired actions from a user of the system 800. Input devices 802 can include, for example, a mouse, a keyboard, a touchscreen, a touchpad, a microphone, or other suitable input user input devices. In some embodiments, the system 800 further includes a display 804 configured to display various types of output from the system 800, such as, for example, images of the photos taken by an automated imaging system, images analyzed by one or more software modules described herein, graphical illustrations of data analyzed by one or more software modules described herein, textual illustrations of data analyzed by one or more software modules described, or combinations thereof. In some embodiments, the CPU 810 executes the data analysis module 835 stored in the persistent storage 830 to analyze a set of images stored in memory 820. The analysis can be reported to the user via the display 804.

It shall be appreciated that the components of the system 800 can be configured in many different ways. For example, although illustrated as being contained within a single device, various aspects of the system 800 can be distributed across multiple computing devices. Moreover, various aspects of the system 800, such as the data analysis module 835, can be stored on a remote server rather than within the persistent storage 830 of the system 800. While computer systems configured as described above can be used to support operations of the methods described herein, those skilled in the art will appreciate that the facility may be implemented using devices of various types and configurations, and having various components.

EXAMPLES

Several aspects of the present technology are set forth in the following examples.

Example 1

Figure 9:
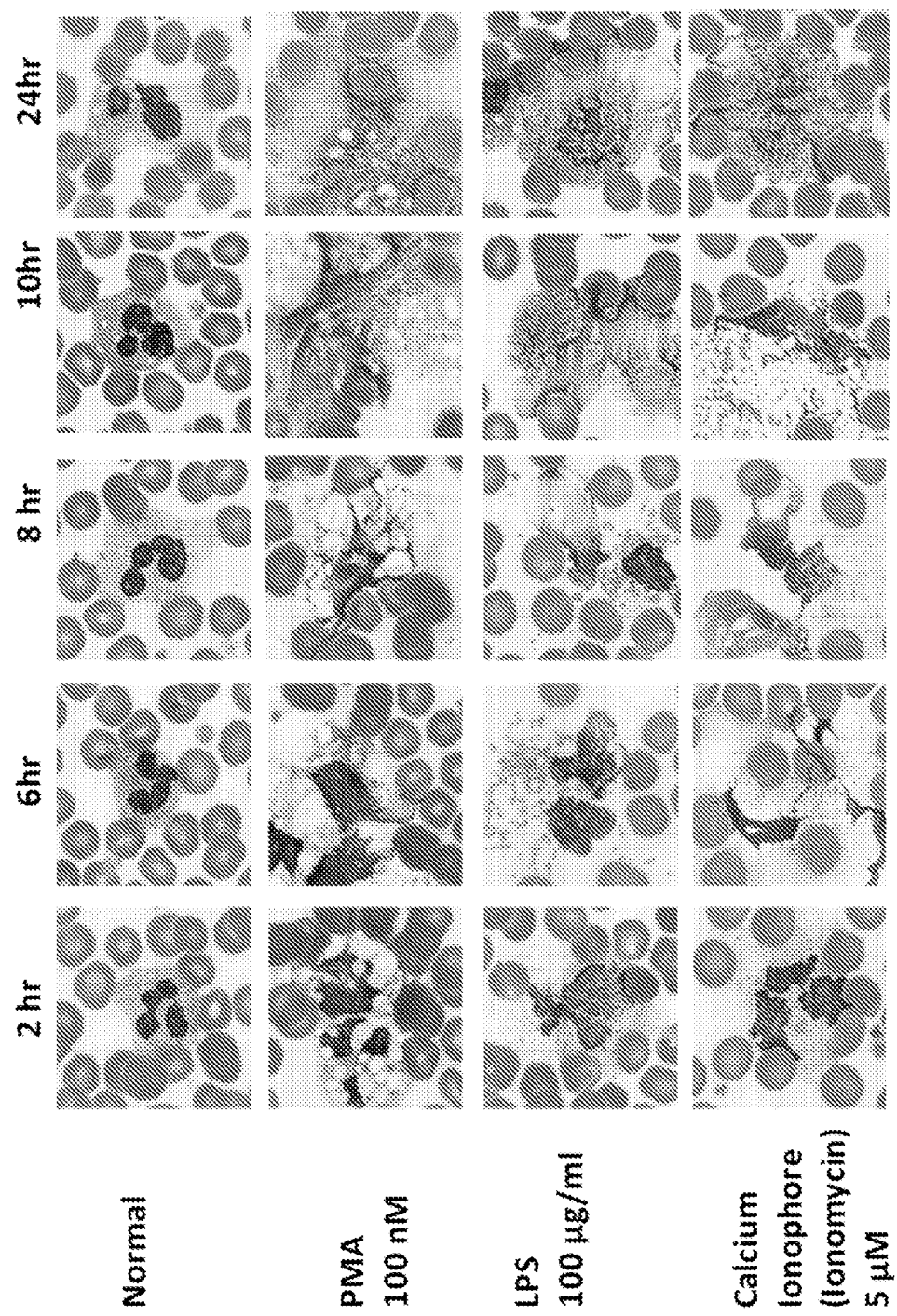
FIG. 9 is a series of images showing various stages of NET formation in accordance with embodiments of the present technology.

In a first example to confirm the formation of and identification of NETs in blood, NETs were induced in blood samples by incubating the sample at 37 degrees Celsius for up to 24 hours with phorbol-12-myristate-13-acetate (PMA), lipopolysaccharide (LPS), and ionomycin, in EDTA-whole blood from normal donors. Smears were prepared at 30-minute intervals for 24 hours. Manual differentials were analyzed by CellaVision® to form a library of images of the cells at various stages (CellaVision® classified the NET like cells as smudge cells, as previously described herein). FIG. 9 includes select images of the cells at various time intervals, showing specific morphological features/changes during NET maturation. NET formation followed a typical order of morphological changes, including vacuolation, nuclear decondensation, degranulation, and chromatin ejection. Normal control without PMA, LPS, or ionomycin did not show significant changes in neutrophil morphology with incubation up to 24 hours. The resultant library was then used to train an artificial intelligence architecture for rapidly identifying NETs in blood smears, as described elsewhere herein.

Example 2

Figure 10A:
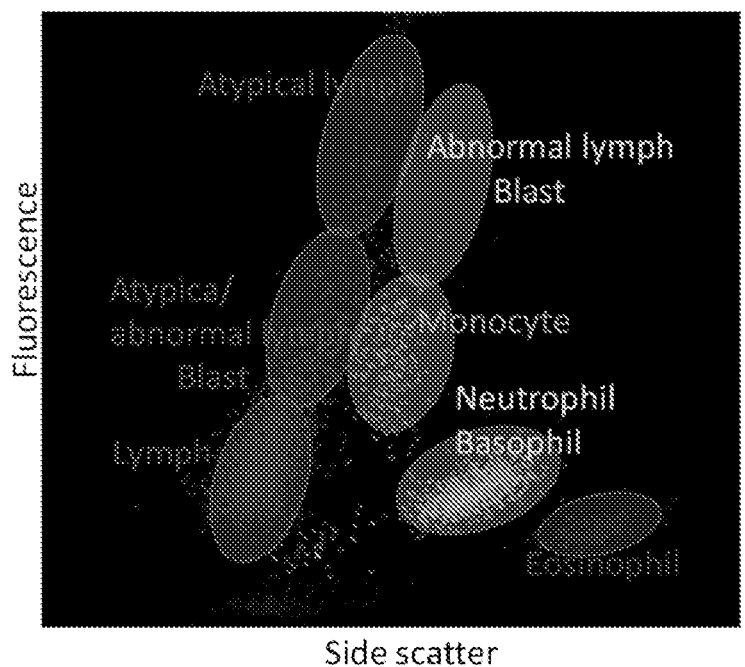
FIGS. 10A and 10B are schematic graphical illustrations of CBC scattergrams.
Figure 10B:
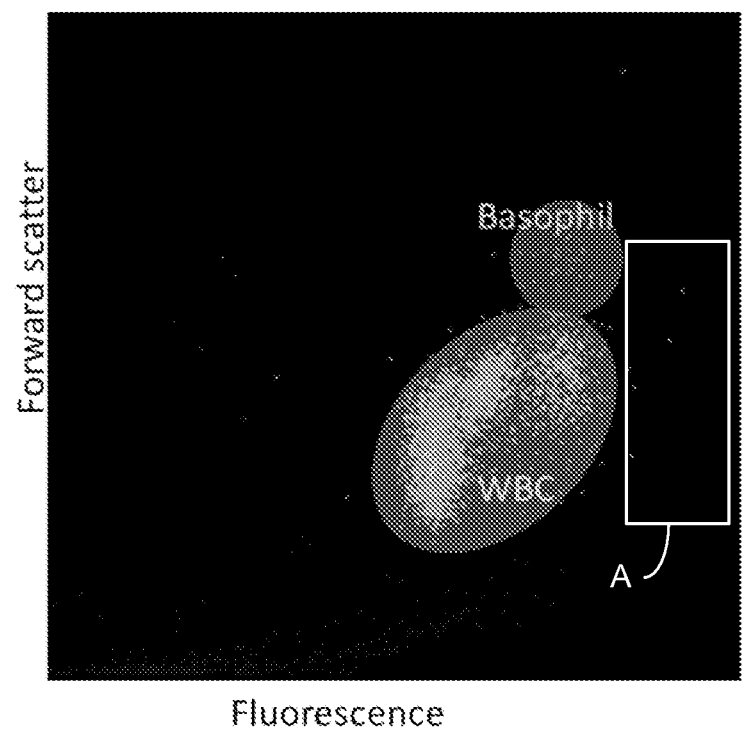

Another test was conducted to confirm the presence of NETs in blood based on a CBC scattergram. FIG. 10A is a schematic representation of a CBC scattergram plot measuring side scatter (SSC) vs. fluorescence. FIG. 10B is a schematic representation of a CBC scattergram plot measuring fluorescence vs. forward scatter (FSC). As illustrated in FIGS. 10A and 10B, different types of cells appear in different areas of the scattergram plots. To confirm if NETs could be identified in a CBC scattergram, NET formation was induced with various triggers described in Example 1 (e.g., PMA and LPS) in EDTA-whole blood from normal donors. The blood smears were then run through an automated hematology analyzer to generate a scattergram plot. The resultant scattergram plots were compared against a control group NL. As will be described below with respect to FIGS. 11A-13, NETs occupy a unique area/position on the CBC scattergram that has not been previously associated with a specific cell type or as an area of interest. The area is marked with box A in FIG. 10B.

Figure 11A:
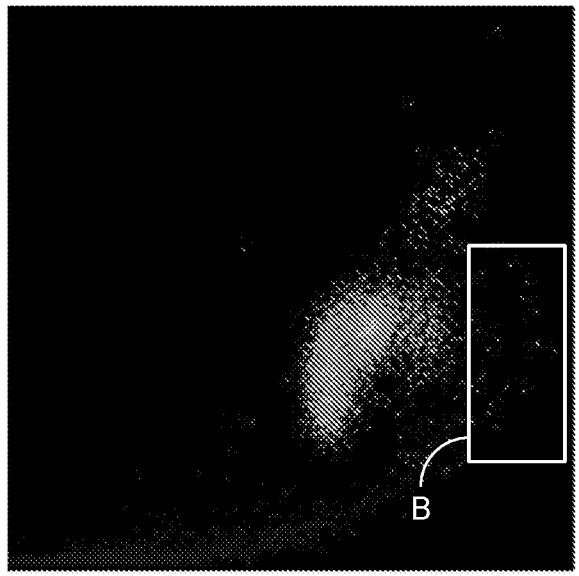
FIGS. 11A-11D are series of images depicting scattergram plots and compare blood treated with PMA versus a control, in accordance with embodiments of the present technology.
Figure 11B:
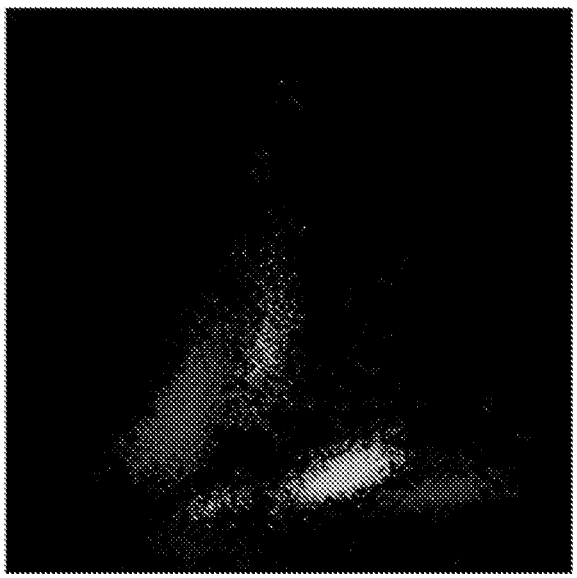
Figure 11C:
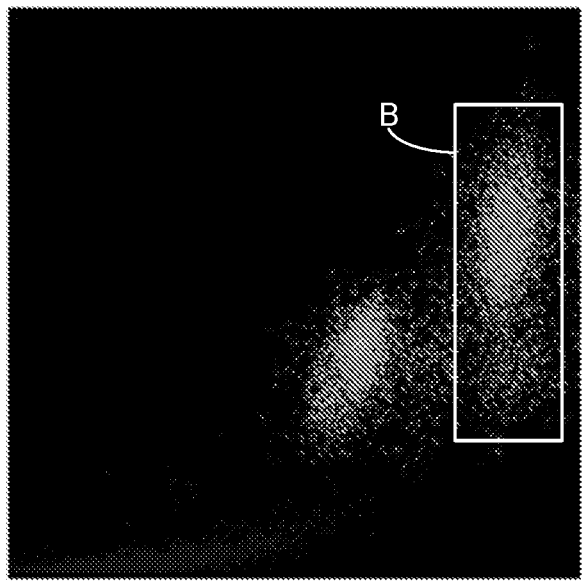
Figure 11D:
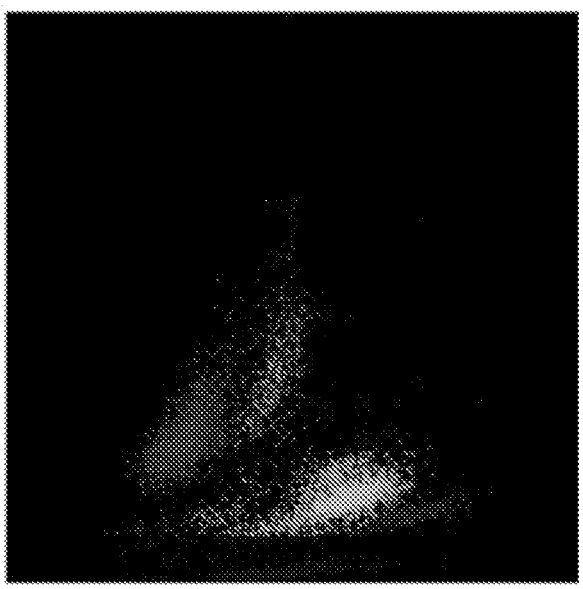
Figure 12A:
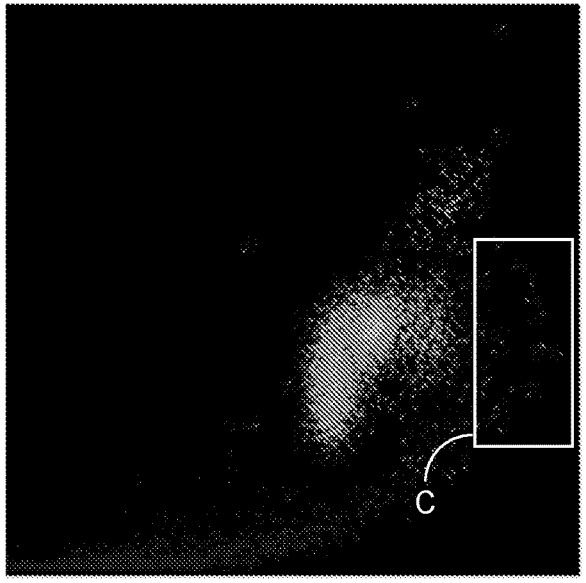
FIGS. 12A-12D are series of images depicting scattergram plots and compare blood treated with LPS versus a control, in accordance with embodiments of the present technology.
Figure 12B:
Figure 12C:
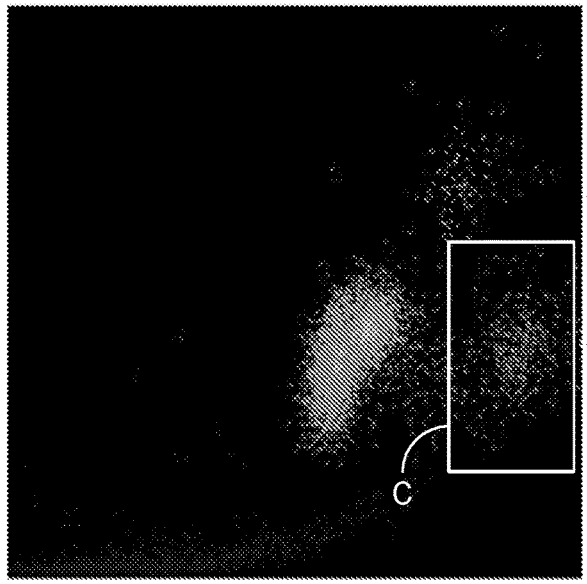
Figure 12D:
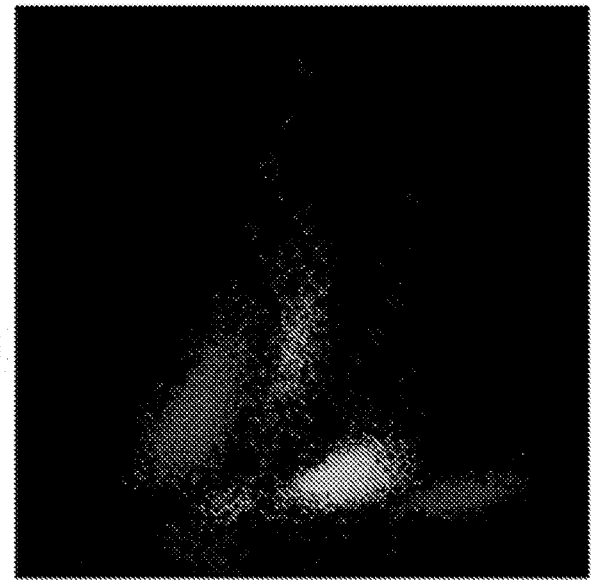
Figure 13:
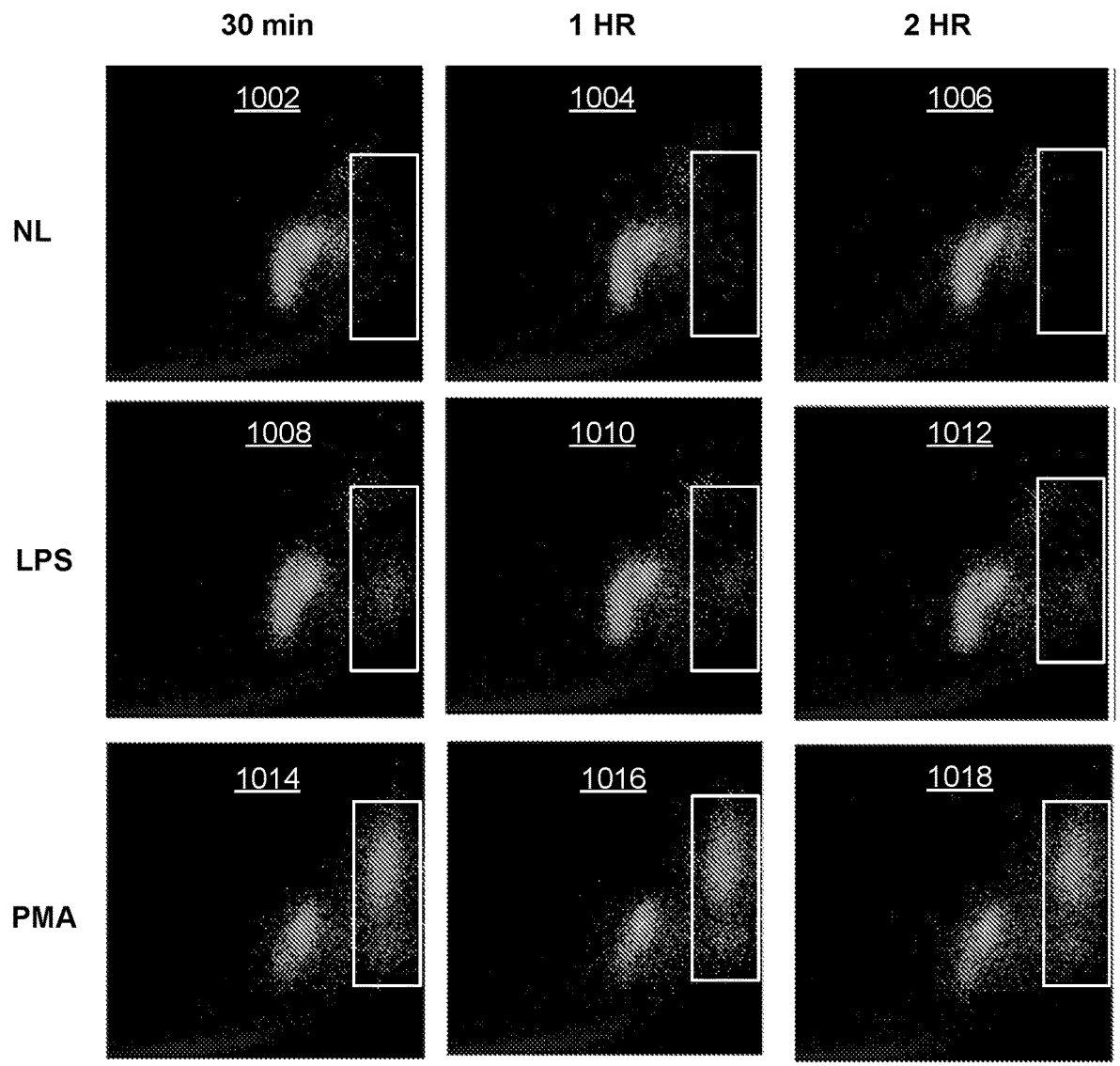
FIG. 13 a series of images of fluorescence vs. FSC scattergrams of a control, LPS treated blood, and PMA treated blood taken at various time intervals, in accordance with embodiments of the present technology.
Figure 14:
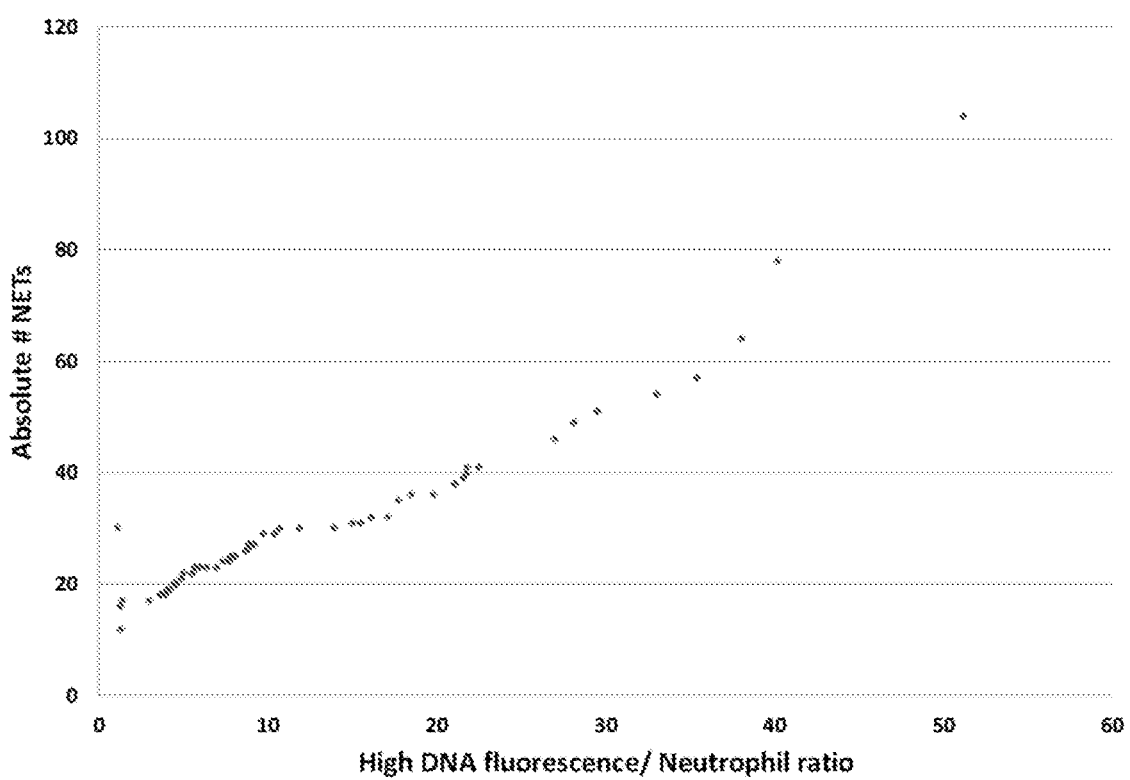
FIG. 14 is a graph illustrating the positive correlation between high DNA fluorescence scatter and absolute number of NETs.

FIGS. 11A-11D includes images of scattergram plots comparing blood treated with PMA versus a control NL. In particular, FIG. 11A illustrates a fluorescence vs. FSC scattergram of normal (e.g., healthy) blood. FIG. 11B illustrates a fluorescence vs. FSC scattergram of normal blood. FIG. 11C illustrates a fluorescence vs. FSC scattergram of same normal blood treated with PMA. FIG. 11D illustrates a fluorescence vs. FSC scattergram of PMA treated blood. The FSC scattergram of PMA treated blood (FIG. 11C) illustrates a marked increase in cells (e.g., NETs) contained within box B relative to the FSC scattergram of untreated blood cells (FIG. 11A). FIGS. 12A-12D includes images of scattergram plots comparing blood treated with LPS versus untreated control blood from same donor. In particular, FIG. 12A illustrates a SSC vs. fluorescence scattergram of normal (e.g., healthy) blood. FIG. 12B illustrates a SSC vs. fluorescence scattergram of normal blood. FIG. 12C illustrates a SSC vs. fluorescence scattergram of LPS treated blood. FIG. 12D illustrates a SSC vs. fluorescence scattergram of PMA treated blood. The FSC scattergram of PMA treated blood (FIG. 12C) illustrates an increase in cells (e.g., NETs) contained within box C relative to the FSC scattergram of control (untreated) blood cells (FIG. 12A). FIG. 13 includes a series of images of fluorescence vs. FSC scattergrams of (1) a control NL taken at time intervals of 30 minutes, 1 hour, and 2 hours (labeled 1002, 1004, and 1006, respectively), (2) LPS treated blood taken at time intervals of 30 minutes, 1 hour, and 2 hours (labeled 1008, 1010, 1012, respectively), and (3) PMA treated blood taken at time intervals of 30 minutes, 1 hour, and 2 hours (labeled 1014, 1016, 1018, respectively). Referring collectively to FIGS. 11A-13, the formation of NETs can be identified in a CBC scattergram, particularly in FSC scattergrams. Moreover, NETs occupy a specific area (e.g., as represented by box A in FIG. 10B, box B in FIG. 11C, box C in FIG. 12C) in a CBC scattergram that has not been previously associated with a specific cell type or as an area of interest. Accordingly, the present technology includes identifying, based on a CBC scattergram, the presence of NETs in a biological sample. FIG. 14 is a graph illustrating the positive correlation between high DNA fluorescence scatter (events in NETs window on the CBC scattergram) normalized to neutrophil count and absolute number of NETs (as per morphology characterization of Wright Giemsa staining of peripheral blood smears, images captured by CellaVision®).

Example 3

Figure 15:
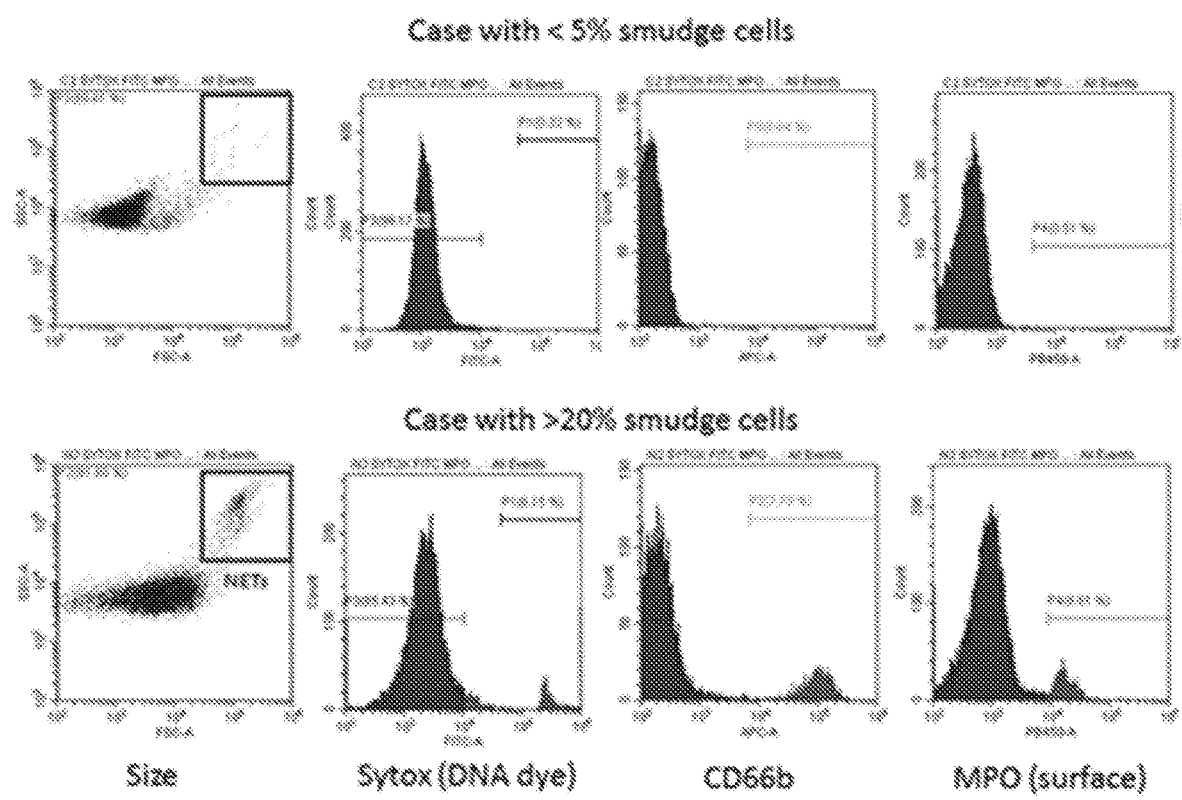
FIG. 15 includes a series of graphs depicting flow cytometry analysis of biological samples containing less than 5% smudge cells and biological samples containing greater than 20% smudge cells that are a majority NETs, in accordance with embodiments of the present technology.

A retrospective study was conducted on peripheral blood smears analyzed with the Cellavision® Hematology Autoanalyzer to correlate the formation of NETs with various conditions, including infections that can lead to sepsis. As previously noted, automated imaging systems such as the Cellavision® Hematology Autoanalyzer classify unrecognizable cells and/or cell remnants as smudge cells, which, as discussed herein, can include NETs and/or degenerating lymphocytes (DL). The study was designed to include a first group containing smears with greater than 20% smudge cells against a control group containing smears with less than 5% smudge cells. The first group was further divided into a subset having a majority of NETs and a subset having a majority of DLs. The group of smears having greater than 20% smudge cells was subclassified into NETs vs. DL based on the review of a hematopathologist blinded to clinical data. The presence of NETs was then confirmed by immunohistochemistry with myeloperoxidase (MPO) and neutrophil elastase. In addition, leukocyte alkaline phosphatase (LAP) staining and scores were calculated for 10 random samples of cells identified as NETs and 10 random samples of cells identified as DLs. The DLs had an average LAP score of 103.3 and the NETs had an average LAP score of 172.1 with a t-test p value of 0.00087, indicating NETs stain stronger for LAP. Furthermore, NETs and DL samples (6 NET samples and 6 DL samples) were analyzed by flow cytometry with Sytox Green (nuclear stain), neutrophil marker CD66b, leukocyte marker CD45, and extracellular MPO to confirm the NET vs. DL identity. The results of the flow cytometry analysis are illustrated in FIG. 15. Several features used to differentiate DLs and NETs are outlined in Table 1.

TABLE 1

| Differences Between NETs and DLs | | | |
| --- | --- | --- | --- |
| Method | Criteria | DL | NETs |
| Morphology | Presence of Cytoplasm | − | − |
| | Presence of Nuclear Segmentation | − | + (early) |
| | Presence of Dense Chromatin | + | − |
| | Presence of Chromatin Projections | − | + |
| Immunohistochemistry | Myeloperoxidase | − | + |
| | Neutrophil Elastase | − | + |
| | Leukocyte Alkaline Phosphatase Score | − | + |
| Flow Cytometry | Surface DNA | + | + |
| | Surface CD66b | − | + |
| | Surface MPO | − | + |

The smudge cells were then compared against the control group to determine the prevalence of certain conditions. More specifically, the groups were reviewed for bacterial infections, viral infections, HIV, liver disease, lymphoproliferative disorders, myeloproliferative disorders, solid organ malignancies, solid organ transplant, CKD, thrombosis, sickle cell disease, and autoimmune disorders. As set forth in Table 2, the group with greater than 20% smudge cells had significantly higher incidence of both bacterial and viral infections.

TABLE 2

Conditions Associated with High Percentage versus Low Percentage Smudge Cells

| Conditions | Smudge cells <5% n = 60 | Smudge cells >20% n = 91 | t-test |
|---|---|---|---|
| Bacterial Infection n (%) | 13 (22%) | 42 (42%) | p = 0.0070* |
| Viral Infection n (%) | 3 (5%) | 14 (14%) | p = 0.049* |
| CKD n (%) | 22 (37%) | 26 (26%) | p = 0.17 |
| Lymphoprolifative Dx n (%) | 6 (10%) | 15 (15%) | p = 0.36 |
| Myeloproliferative Dx n (%) | 11 (18%) | 10 (10%) | p = 0.15 |
| Transplant n (%) | 12 (20%) | 10 (10%) | p = 0.096 |
| Autoimmune Disorder n (%) | 4 (7%) | 7 (7%) | p = 0.95 |
| Solid Malignancy n (%) | 21 (35%) | 23 (23%) | p = 0.10 |
| Sickle Cell Disease n (%) | 2 (3%) | 6 (6%) | p = 0.43 |
| VTE/ATE n (%) | 5 (8%) | 12 (12%) | p = 0.46 |
| HIV n (%) | 1 (2%) | 8 (8%) | p = 0.05 |
| Liver Dx n (%) | 9 (15%) | 13 (13%) | p = 0.71 |

The subset of the first group containing majority NETs were also compared with the subset of the first group containing majority DLs. More specifically, the subsets were reviewed for bacterial infections, viral infections, HIV, liver disease, lymphoproliferative disorders, myeloproliferative disorders, solid organ malignancies, solid organ transplant, CKD, thrombosis, sickle cell disease, and autoimmune disorders. The resultant data showed that cases with a higher percentage of NETs had increased incidence of bacterial infections, viral infections, transplant complications, autoimmune disorders, sickle cell disease, HIV, and liver disease, whereas cases with a high percentage of DLs were associated with increased incidence of lymphoproliferative disorders and chronic kidney disease (CKD) (see Table 3).

TABLE 3

Conditions Associated with High Percentage of NETs versus DL

| Condition | Majority NETs n = 81 | Majority DL n = 10 | T-test |
|---|---|---|---|
| Bacterial Infection, n (%) | 40 (44%) | 2 (20%) | p = 0.018 |
| Viral Infection, n (%) | 12 (13%) | 2 (20%) | p = 0.67 |
| CKD, n (%) | 20 (22%) | 6 (60%) | p = 0.049 |
| Lymphoproliferative Dx, n (%) | 9 (10%) | 6 (60%) | p = 0.014 |
| Myeloproliferative Dx, n (%) | 6 (7%) | 4 (40%) | p = 0.073 |
| Transplant, n (%) | 10 (11%) | 0 (0%) | p = 0.0012 |
| Autoimmune Disorders, n (%) | 7 (8%) | 0 (0%) | p = 0.0074 |
| Solid Malignancy, n (%) | 20 (22%) | 3 (30%) | p = 0.63 |
| Sickle Cell Disease, n (%) | 6 (7%) | 0 (0%) | p = 0.013 |
| VTE/ATE, n (%) | 10 (11%) | 2 (20%) | p = 0.53 |
| HIV, n (%) | 8 (9%) | 0 (0%) | p = 0.0041 |
| Liver Dx, n (%) | 13 (14%) | 0 (0%) | p = 0.0002 |

Classic CBC parameters between the control group and the subset of the first group with the high percentage of NETs were also compared. Data from this study is shown in Table 4. Notably, the white blood cell count was within normal limits in both groups with no significant differences. This indicates that the high percentage of NETs seen with infections (e.g., bacterial or viral) is an earlier marker that precedes elevation of WBCs. Accordingly, as discussed above, the formation of NETs can be used as an early indicator for infection and/or sepsis before the elevation of WBCs in response to bacterial and/or viral infections. Thus, detecting and counting NETs in peripheral blood smears allows early detection of infection and can be incorporated in sepsis screening scores to prevent sepsis.

TABLE 4

Cases with High Percentage NETs Exhibit Normal CBC

| CBC parameters | <5% NETs | High % NETs | T Test |
|---|---|---|---|
| WBC | 7.4 | 8.5 | p = 0.22 |
| Neutrophil | 5.2 | 4.5 | p = 0.29 |
| Lymphocyte | 1.4 | 2.8 | p = 0.00023 |
| Monocyte | 0.57 | 0.75 | p = 0.11 |
| LDH | 500 | 620 | p = 0.52 |
| Hb | 9.8 | 11 | p = 0.058 |
| Platelet | 180 | 220 | p = 0.081 |
| PTT | 29 | 35 | P = 0.064 |

Example 4

Another study was performed to study the correlation of high NET percent on blood smears with infection. Similar to the methods described with respect to Example 3, NETs were distinguished from DLS based on morphologic characteristics, immunohistochemistry, immunofluorescence and flow cytometry. Smears with greater than 20% smudge cells were classified morphologically as NETs vs. DLS and compared to a control group of less than 5% smudge cells. Medical chart review performed by blinded investigators, included patient demographics, presence of bacterial or viral infection occurring less than one week of sample collection, and other comorbidities. Statistical analyses included two-sided t-test and chi-square.

Figure 16:
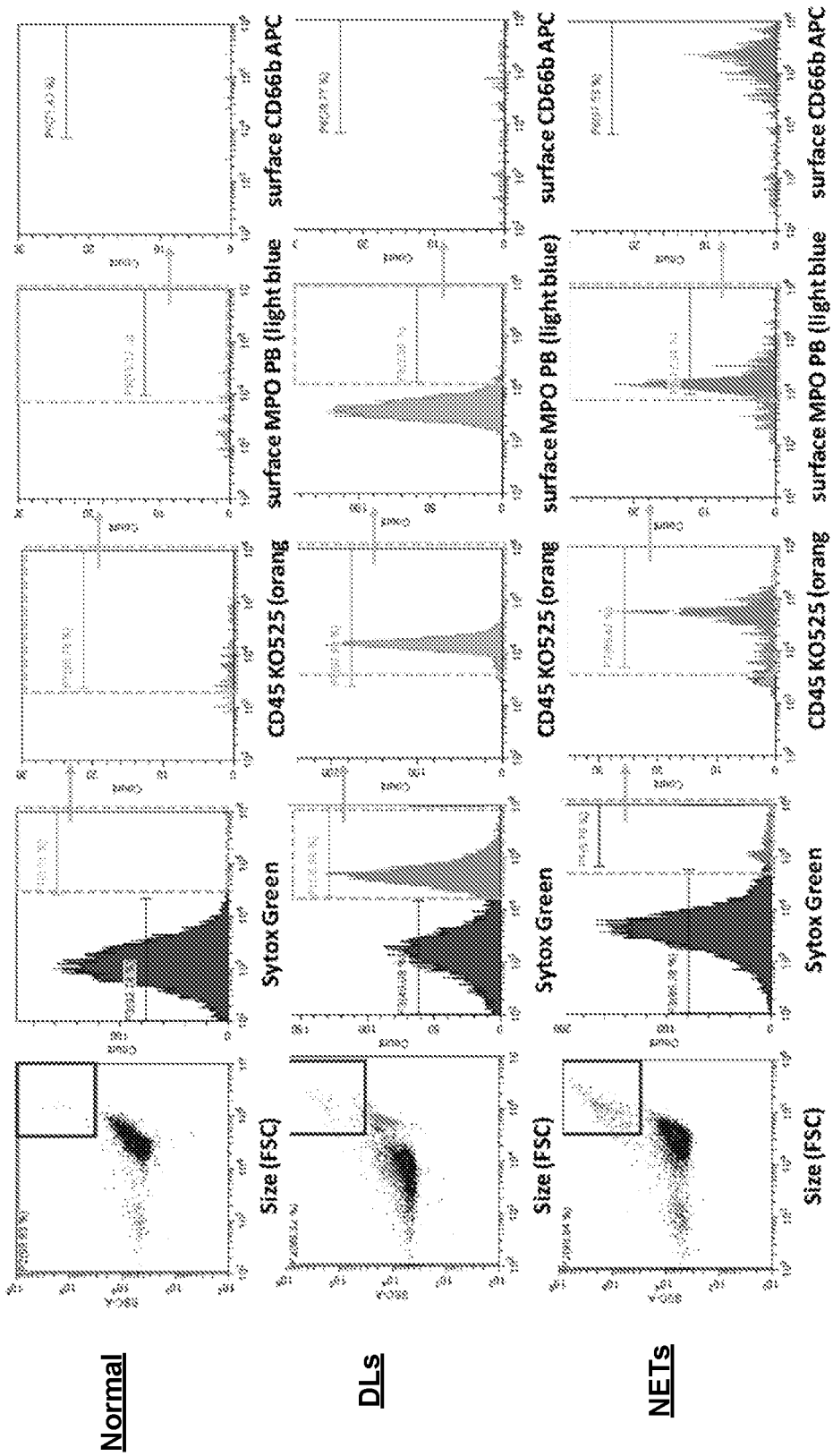
FIG. 16 includes a series of graphs depicting flow cytometry analysis of biological samples containing less than 5% smudge cells and biological samples containing greater than 20% smudge cells and classified as either degenerating lymphocytes or NETs, in accordance with embodiments of the present technology.
Figure 17:
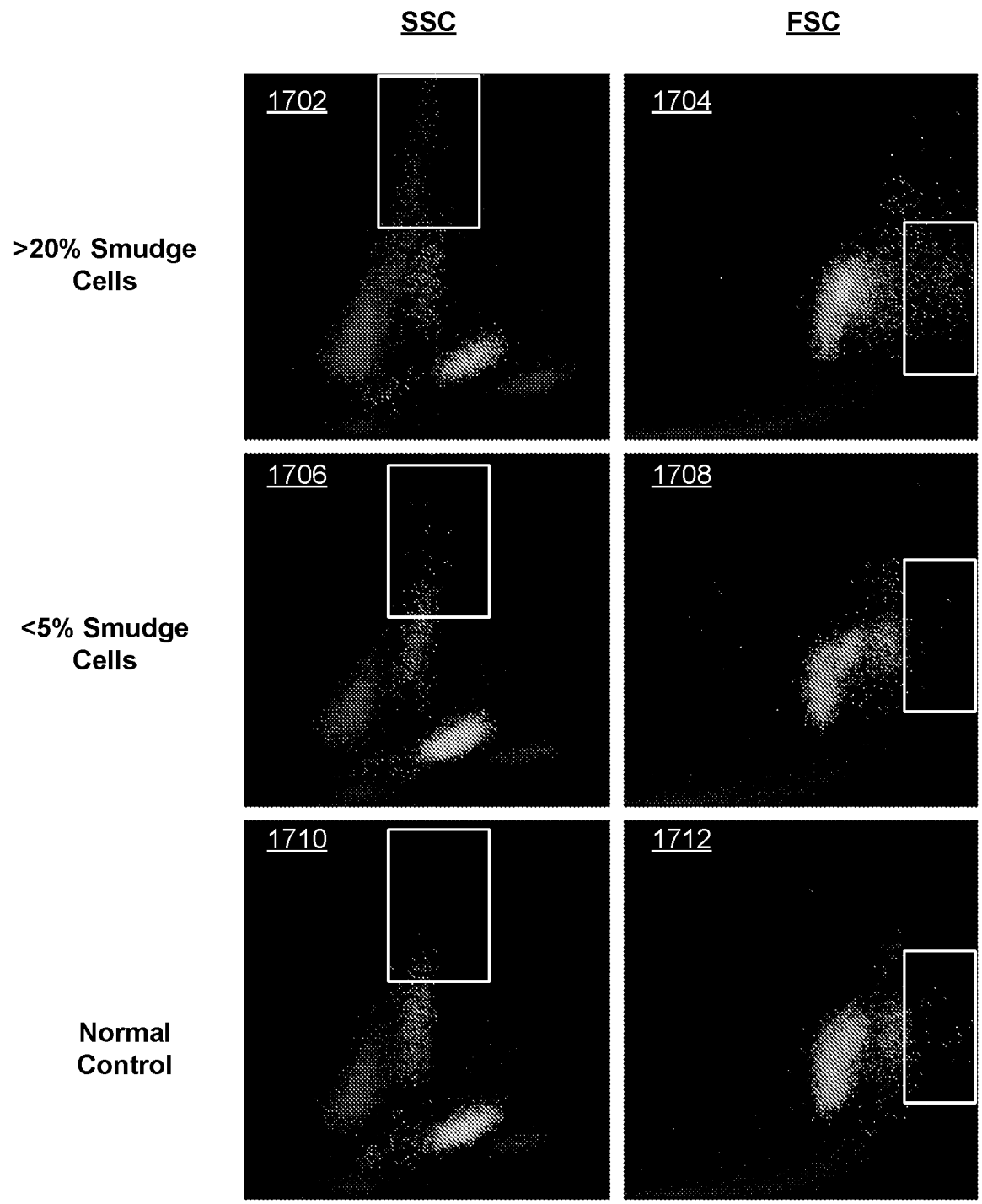
FIG. 17 is a series of images of FSC and SSC scattergrams of biological samples containing less than 5% smudge cells and biological samples containing greater than 20% smudge cells and classified as either degenerating lymphocytes or NETs, in accordance with embodiments of the present technology.

Samples were first divided between the study group (greater than 20% smudge cells; n=96) and the test group (less than 5% smudge cells; n=59). Within the study group, 88 samples were morphologically designated as NETs and 8 samples were morphologically designated as DLs. Following morphological classification, the designation of NET vs. DL was confirmed using various techniques. For example, smears from within the NET classification of the study group stained strongly with MPO, neutrophil elastase, leukocyte alkaline phosphatase, whereas smears from within the DL classification of the study group did not. On Wright-Giemsa stain, cell remnants that were morphologically classified as NETs also stained for Sytox-Green. On flow cytometry, NETs are large and display extracellular DNA and MPO. The flow cytometry results are shown in FIG. 16. The aggregated scattergrams are shown in FIG. 17, with both SSC and FSC plots for the study group (images 1702 and 1704, respectively), the test group (images 1706 and 1708, respectively), and a normal control (images 1710 and 1712, respectively).

The samples included in the study group and test group were then reviewed to identify the presence of various pathological conditions. The results are displayed in Table 5 below. As indicated, the presence of NETs in the study group of greater than 20% smudge cells showed a significant correlation with bacterial or viral infections, as compared to the DL classification and the test group. The majority of the DL cases were CLL, explaining the significantly higher WBC.

TABLE 5

Conditions Associated with High Percentage of NETs versus DL

| | ≤5% Smudge Cells | ≥20% Smudge Cells n = 96 | | T-test ≤5% vs. ≥20% Smudge Cells | T-test ≤5% vs. ≥NETs | T-test ≤5% vs. DLs | T-test NETs vs. DLs |
|---|---|---|---|---|---|---|---|
| | Cells n = 59 | NETs n = 88 | DL n = 8 | | | | |
| Bacterial Infection, n (%) | 11 (18.6%) | 35 39.8%) | 1 (12.5%) | 0.0091 | 0.0045 | 0.66 | 0.073 |
| Viral Infection (HIV, HBV, HCV) n (%) | 8 (13.6%) | 29 33.0%) | 2 (25.0%) | 0.0085 | 0.0081 | 0.53 | 0.663 |
| Lymphoproliferative Disorder, n(%) | 12 (20.3%) | 6 (6.81%) | 5 (62.5%) | 0.16 | 0.17 | 0.17 | 0.019 |
| Myeloproliferative/MDS, n(%) | 9 (15.3%) | 5 (5.7%) | 2 (25.0%) | 0.15 | 0.076 | 0.58 | 0.28 |
| VTE/ATE, n(%) | 5 (8.5%) | 10 (11.4%) | 1 (12.5%) | 0.544 | 0.56 | 0.76 | 0.93 |
| WBC (×10$^9$/L), mean (SD) | 7.4 (4.8) | 8.5 (5.75) | 84.05 (69.6) | 0.014 | 0.18 | 0.017# | 0.018# |
| Neutrophil (×10$^9$/L), mean (SD) | 5.24 (4.09) | 4.50 (4.0) | 5.35 (5.5) | 0.33 | 0.28 | 0.959 | 0.68 |
| Age, median yrs (IQR) | 61 (68.1-43.5) | 48.0 (63.1-7.3) | 69.6 (80-65.2) | | | | |
| % Female | 42.4% | 44.3% | 50% | | | | |

Example 5

To test the concept of DS-CNN in identifying and classifying NETs versus degenerating lymphocytes, a neural network architecture with DS-CNN was loaded onto a computer with a 1.4 GHz Intel Core i5 dual-core CPU. The DS-CNN architecture was a 28-layer architecture with 3×3 depthwise separable convolutions. All layers were followed by batchnorm and ReLU nonlinearity (except for the final fully connected layer which had no nonlinearity and fed into a softmax layer for classification). The width multiplier α was set at 1. The input image resolution was 224×224 pixels, the training batch size was 10, the validation batch size was 100, and the learning rate was 0.01. Training was done for 4000 iterations.

The training and test datasets were accumulated from the automated imaging system CellaVision. The training dataset included two classes of cell types: 706 NETs and 550 degenerating lymphocytes, for a total of 1256 unique training images. To account for the low sample size of degenerating lymphocytes, mirror images of some of the degenerating lymphocytes were added to the training dataset to increase the total number of degenerating lymphocytes to 706. The test dataset included 70 images of NETs and 70 images of degenerating lymphocytes. All cells in the training and test datasets were Wright Giemsa stained with a magnification of 100×, with each cell displayed on a 360×366 pixel JPEG image.

Figure 18A:
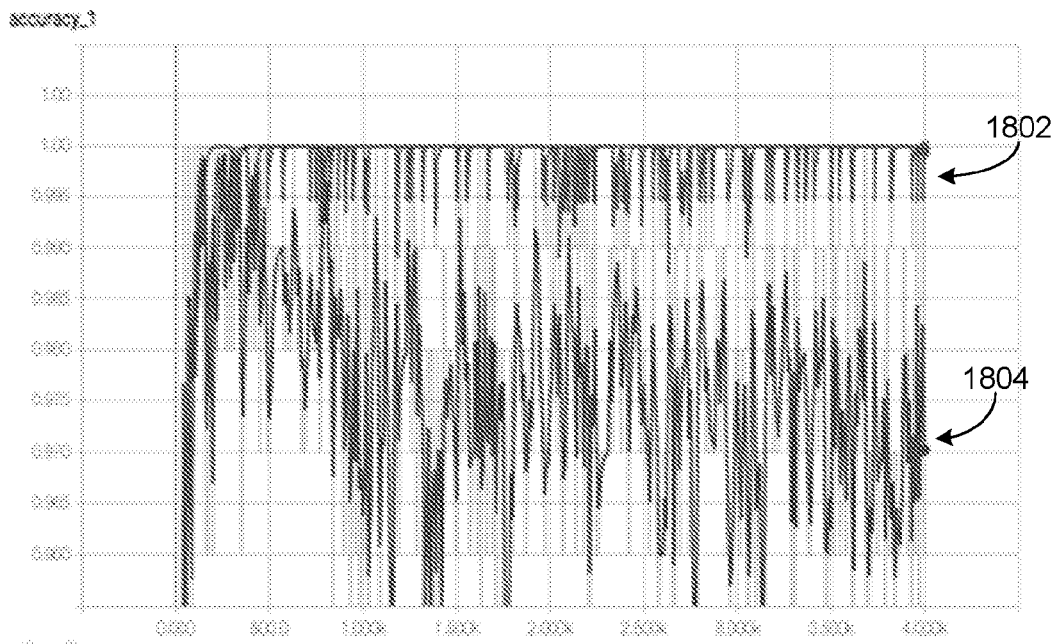
FIG. 18A is a graph depicting the accuracy of a training set and validation set used to train and test a depthwise separable convolutional neural network architecture in accordance with embodiments of the present technology.
Figure 18B:
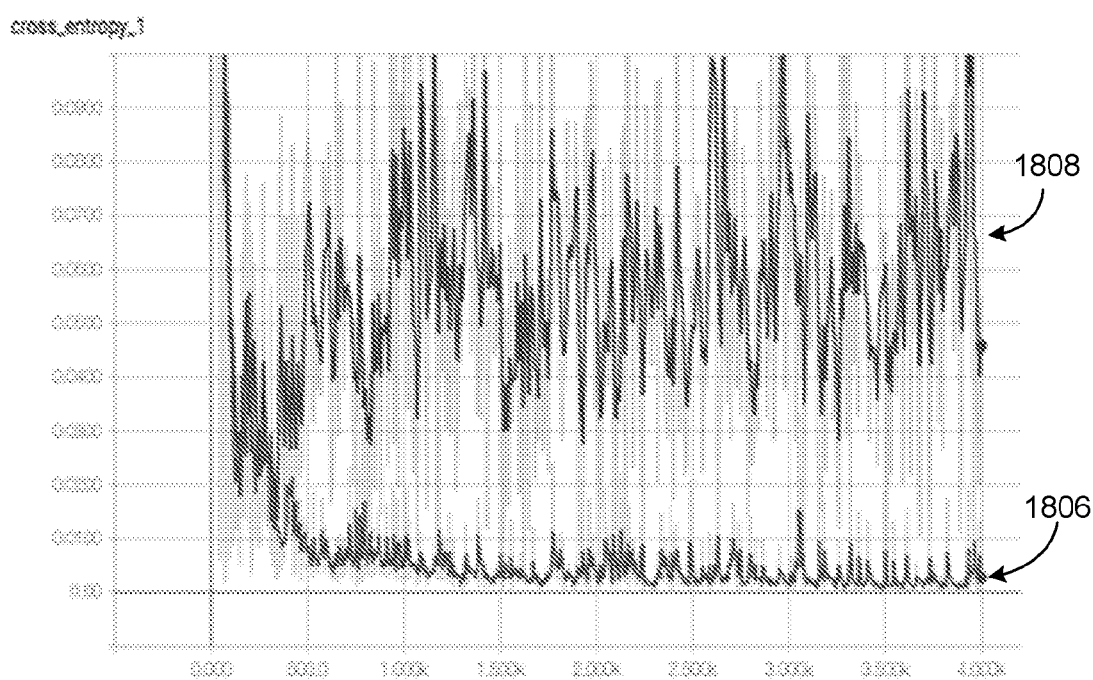
FIG. 18B is a graph depicting the cross entropy of a training set and validation set used to train and test a depthwise separable convolutional neural network architecture in accordance with embodiments of the present technology

The training period for the DS-CNN was approximately 30 minutes. The final training set accuracy was 100% and final cross-validation accuracy was 97%. FIG. 18A illustrates the accuracy of the DS-CNN architecture, and FIG. 18B illustrates the cross entropy of the DS-CNN architecture. In FIG. 18A, line 1802 represents the training set, and line 1804 represents the validation set. In FIG. 18B, line 1806 represents the training set, and line 1808 represents the validation set. The cross entropy of the training and validation test set was 1.35e$^{-3}$ and 0.045, respectively. The overall sensitivity and specificity to detect NETs is reported in Table 6. The resulting model size as 17 MB.

TABLE 6

Accuracy of DS-CNN Architecture in Classifying NETs vs. Lymphocytes

| | NETs | Lymphocyte |
|---|---|---|
| NETs | 70 | 1 |
| Lymphocytes | 0 | 69 |
| Sensitivity | 100% | 98.57% |

Examples 6-104

6. A method for identifying neutrophil extracellular traps in a peripheral blood smear using a computing system, the method comprising:
  receiving one or more images of a biological sample, wherein the imaged biological sample includes white blood cells;
  analyzing morphological features of the white blood cells in the one or more images using a depthwise separable convolutional neural network; and
  based at least in part on the morphological features of the white blood cells, indicating whether the one or more images include neutrophil extracellular traps.

7. The method of example 6, further comprising providing a confidence score for each of the one or more images, wherein the confidence score reflects the likelihood that an image contains a neutrophil extracellular trap.

8. The method of example 6 or 7, further comprising indicating whether the one or more images include degenerating lymphocytes.

9. The method of any of examples 6-8, further comprising sorting the one or more images based on whether the one or more images include neutrophil extracellular traps.

10. The method of any of examples 6-9 wherein the one or more images comprises a dataset of images corresponding to a biological sample taken from a single subject.

11. The method of example 7 wherein indicating whether the one or more images includes neutrophil extracellular traps further comprising indicating the total number of neutrophil extracellular traps identified in the dataset of images and/or indicating a ratio of neutrophil extracellular traps to other white blood cells.

12. The method of example 7 or 8 wherein the presence of neutrophil extracellular traps in the dataset of images is indicative of sepsis in the subject.

13. The method of any of examples 6-12 wherein the depthwise separable convolutional neural network is pre-trained to identify neutrophil extracellular traps based on morphology.

14. The method of method of any of examples 6-14 wherein the computing system is an automated imaging system.

15. The method of any of examples 6-14 wherein the computing system is a mobile device.

16. A system for identifying neutrophil extracellular traps in peripheral blood smears, the system comprising a computer readable medium with instructions that, when executed:
   receive one or more images of a biological sample, wherein the imaged biological sample includes white blood cells;
   analyze morphological features of the white blood cells in the one or more images using a depthwise separable convolutional neural network; and
   based at least in part on the morphological features of the white blood cells, indicate whether the one or more images include neutrophil extracellular traps.

17. The system of example 16 wherein the instructions, when executed, provide a confidence score for each of the one or more images, and wherein the confidence score reflects the likelihood that an image contains a neutrophil extracellular trap.

18. The system of example 17 or 17 wherein the instructions, when executed, indicate whether the one or more images include degenerating lymphocytes.

19. The system of any of examples 16-18 wherein the instructions, when executed, further sort the one or more images based on whether the one or more images include neutrophil extracellular traps.

20. The system of any of examples 16-19 wherein the one or more images comprises a dataset of images corresponding to a biological sample taken from a single subject.

21. The system of example 20 wherein the instructions, when executed, indicate the total number of neutrophil extracellular traps identified in the dataset of images and/or indicate a ratio of neutrophil extracellular traps to other white blood cells.

22. The system of example 20 or 21 wherein the presence of neutrophil extracellular traps in the dataset of images is indicative of sepsis in the subject.

23. The system of any of examples 16-22 wherein the depthwise separable convolutional neural network is pre-trained to identify neutrophil extracellular traps based on morphology.

24. The system of any of examples 16-23 wherein the computer readable medium is operable with an automated imaging system.

25. The system of any of examples 16-23 wherein the computer readable medium is operable with a mobile device.

26. An automated imaging system for analyzing peripheral blood smears, the automated imaging system comprising:
   a computer readable medium storing a depthwise separable convolutional neural network, wherein the depthwise separable convolutional neural network is configured to analyze the morphology of a dataset of images and sort the images based on whether the images contain neutrophil extracellular traps.

27. The automated imaging system of example 26 wherein the depthwise separable convolutional neural network is pre-trained using a set of training images.

28. The automated imaging system of example 27 wherein the set of training images includes a first plurality of images and a second plurality of images, and wherein the first plurality of images includes images of a stained biological sample having neutrophil extracellular traps, and wherein the second plurality of images includes images of a stained biological sample without neutrophil extracellular traps.

29. A method in a computing system for training a neural network to identify neutrophil extracellular traps in peripheral blood smears, the method comprising:
   receiving a plurality of inputs, wherein the plurality of inputs includes stained images of biological samples, and wherein each individual stained image is associated with a particular target output;
   providing a plurality of observations corresponding to the plurality of inputs, wherein each observation includes the particular target output; and
   using the observations to train the artificial intelligence system to accurately identify neutrophil extracellular traps,
   wherein the neural network includes a depthwise separable convolutional neural network.

30. The method of example 29 wherein the stained images include a first plurality of images and a second plurality of images, and wherein the first plurality of images includes images of a stained biological sample having neutrophil extracellular traps, and wherein the second plurality of images includes images of a stained biological sample without neutrophil extracellular traps.

31. The method of example 29 or 30 wherein the neural network includes a multi-layered architecture.

32. The method of example 31 wherein the neural network includes a 28-layer architecture.

33. The method of example 30 or 31 wherein the first layer is a full convolutional layer, and wherein each subsequent layer is a depthwise separable layer having 3×3 convolutions.

34. The method of any of examples 31-33 wherein one or more of the convolutional layers include one or more feature filters configured to extract one or more features from a region of units using a convolution.

35. The method of example 34, wherein the one or more features includes (1) one or more local features, (2) one or more global features, (3) one or more edges, (4) one or more colors, (5) one or more intensity level, (6) one or more spatial features, and/or (7) one or more shape features.

36. The method of any of examples 29-35 wherein the neural network has a width multiplier $\alpha$ of 1.

37. The method of any of examples 29-35 wherein the neural network has a width multiplier $\alpha$ less than 1.

38. The method of any of examples 29-37, further comprising storing the trained artificial intelligence system on a computer readable medium.

39. A computer readable medium storing an artificial intelligence architecture comprising a depthwise separable convolutional neural network, wherein the depthwise separable convolutional neural network is pre-trained to analyze an image of a stained biological sample and identify neutrophil extracellular traps in the image.

40. The computer readable medium of example 39 wherein the depthwise separable convolutional neural network includes a multi-layered architecture.

41. The computer readable medium of example 40 wherein the depthwise separable convolutional neural network includes a 28-layer architecture.

42. The computer readable medium of example 40 or 41 wherein the first layer is a full convolutional layer, and wherein each subsequent layer is a depthwise separable layer having 3×3 convolutions.

43. The computer readable medium of any of examples 40-42 wherein one or more of the convolutional layers include one or more feature filters configured to extract one or more features from a region of units using a convolution.

44. The computer readable medium of example 43, wherein the one or more features includes (1) one or more local features, (2) one or more global features, (3) one or more edges, (4) one or more colors, (5) one or more intensity level, (6) one or more spatial features, and/or (7) one or more shape features.

45. The computer readable medium of any of examples 39-44 wherein the neural network has a width multiplier α of 1.

46. The computer readable medium of any of examples 39-44 wherein the neural network has a width multiplier α less than 1.

47. A hardware networking component conveying a data structure, the data structure comprising a depthwise separable convolutional neural network, wherein the depthwise separable convolutional neural network is pre-trained to analyze an image of a stained biological sample and identify neutrophil extracellular traps in the image.

48. The hardware networking component of example 47 wherein the depthwise separable convolutional neural network includes a multi-layered architecture.

49. The hardware networking component of example 48 wherein the depthwise separable convolutional neural network includes a 28-layer architecture.

50. The hardware networking component of example 48 or 49 wherein the first layer is a full convolutional layer, and wherein each subsequent layer is a depthwise separable layer having 3×3 convolutions.

51. The hardware networking component of any of examples 48-50 wherein one or more of the convolutional layers include one or more feature filters configured to extract one or more features from a region of units using a convolution.

52. The hardware networking component of any of examples 51 wherein the one or more features includes (1) one or more local features, (2) one or more global features, (3) one or more edges, (4) one or more colors, (5) one or more intensity level, (6) one or more spatial features, and/or (7) one or more shape features.

53. The hardware networking component of any of examples 47-52 wherein the neural network has a width multiplier α of 1.

54. The hardware networking component of any of examples 47-52 wherein the neural network has a width multiplier α less than 1.

55. A method for identifying neutrophil extracellular traps in peripheral blood smears, the method comprising:
staining a biological sample obtained from a peripheral blood smear with a Wright Giemsa stain; and
analyzing morphological features of the stained sample to determine whether the sample contains neutrophil extracellular traps.

56. A method for diagnosing sepsis in a human patient, the method comprising:
receiving a biological sample obtained from a peripheral blood smear taken from the patient;
staining the biological sample; and
analyzing the stained biological sample to identify neutrophil extracellular traps, wherein identifying neutrophil extracellular traps in the biological sample indicates an increased likelihood that the patient has or may develop sepsis.

57. The method of example 56 wherein staining the biological comprises staining the biological sample with a Wright Giemsa stain.

58. The method of example 56 or 57 wherein analyzing the biological sample to identify neutrophil extracellular traps comprises identifying the neutrophil extracellular traps based on morphology.

59. The method of any of examples 56-58 wherein the neutrophil extracellular traps are identified based solely on morphology.

60. A computer-implemented method for identifying neutrophil extracellular traps in blood using a computing system, the method comprising:
obtaining one or more images of a biological sample, wherein the biological sample includes white blood cells;
analyzing one or more morphological features of the white blood cells in the one or more images, wherein analyzing the one or more morphological features includes using an artificial intelligence architecture that includes a depthwise separable convolutional neural network; and
based at least in part on the analysis of the one or more morphological features, indicating whether the one or more images include neutrophil extracellular traps.

61. The computer-implemented method of example 60, further comprising generating a confidence score for each of the one or more images, wherein the confidence score reflects the likelihood that an image contains a neutrophil extracellular trap.

62. The computer-implemented method of example 60 or 61, further comprising indicating whether the one or more images include degenerating lymphocytes.

63. The computer-implemented method of any of examples 60-62, further comprising sorting the one or more images based at least in part on whether the one or more images include neutrophil extracellular traps.

64. The computer-implemented method of any of examples 60-62 wherein the one or more images comprises a dataset of images corresponding to a biological sample taken from a single subject.

65. The computer-implemented method of example 64 wherein indicating whether the one or more images include neutrophil extracellular traps further comprises (i) indicating the total number of neutrophil extracellular traps identified in the dataset of images and/or (ii) indicating a ratio of neutrophil extracellular traps to other white blood cells.

66. The computer-implemented method any of examples 60-65 wherein obtaining the one or more images includes receiving, from an automated imaging system, the one or more images.

67. The computer-implemented method of any of examples 60-65 wherein obtaining the one or more images includes directing an automated imaging system to take the one or more images.

68. The computer-implemented method of any of examples 60-67 wherein the depthwise separable convolutional neural network is trained to identify neutrophil extracellular traps based solely on morphology.

69. The computer-implemented method of any of examples 60-68 wherein the computing system is an automated imaging system, and wherein the automated imaging system includes one or more cameras configured to obtain the one or more images.

70. The computer-implemented method of any of examples 60-68 wherein the computing system is a mobile device, and wherein the mobile device includes one or more cameras configured to obtain the one or more images.

71. The computer-implemented method of any of examples 60-70 wherein the depthwise separable convolutional neural network includes a multi-layered architecture having between 3 and 40 layers.

72. The computer-implemented method of example 71 wherein the first layer is a full convolutional layer, and wherein each subsequent layer is a depthwise separable layer having 3×3 convolutions.

73. The computer-implemented method of example 71 or 72 wherein one or more of the convolutional layers include one or more feature filters configured to extract one or more features from a region of units using a convolution, wherein the one or more filter features includes 1) one or more local features, (2) one or more global features, (3) one or more edges, (4) one or more colors, (5) one or more intensity level, (6) one or more spatial features, and/or (7) one or more shape features.

74. A system for identifying neutrophil extracellular traps in peripheral blood smears, the system comprising:
  a computing device including one or more processors and a non-transitory computer readable medium storing (i) a data analysis module including a depthwise separable convolutional neural network, and (ii) instructions that, when executed by the one or more processors, cause the computing device to perform operations comprising:
    obtaining one or more images of a biological sample, wherein the biological sample includes white blood cells;
    analyzing, via the data analysis module, one or more morphological features of the white blood cells in the one or more images; and
    based at least in part on the one or more analyzed morphological features of the white blood cells, indicating whether the one or more images include neutrophil extracellular traps.

75. The system of example 74 wherein the instructions, when executed, further cause the computing device to perform the operation of providing a confidence score for each of the one or more images, and wherein the confidence score reflects the likelihood that an image contains a neutrophil extracellular trap.

76. The system of example 74 or 75 wherein the instructions, when executed, further cause the computing device to perform the operation of indicating whether the one or more images include degenerating lymphocytes.

77. The system of any of examples 74-76 wherein the instructions, when executed, further cause the computing device to perform the operation of sorting the one or more images based at least in part on whether the one or more images include neutrophil extracellular traps.

78. The system of any of examples 74-77 wherein the one or more images comprises a dataset of images corresponding to a biological sample taken from a single subject.

79. The system of example 78 wherein the instructions, when executed, further cause the computing device to perform the operation of (i) indicating the total number of neutrophil extracellular traps identified in the dataset of images and/or (ii) indicating a ratio of neutrophil extracellular traps to other white blood cells.

80. The system of any of examples 74-79 wherein the operation of obtaining the one or more images includes receiving, from an automated imaging system, the one or more images.

81. The system of any of examples 74-79 wherein the operation of obtaining the one or more images includes directing an automated imaging system to take the one or more images.

82. The system of any of examples 74-81 wherein the depthwise separable convolutional neural network is pre-trained to identify neutrophil extracellular traps based on morphology.

83. The method of any of examples 74-82 wherein the computing device is an automated imaging system, and wherein the automated imaging system includes one or more cameras configured to obtain the one or more images.

84. The method of any of examples 74-82 wherein the computing device is a mobile device, and wherein the mobile dev configured to obtain the one or more images.

85. The system of any of examples 74-84 wherein the depthwise separable convolutional neural network includes a multi-layered architecture having between 3 and 40 layers.

86. The system of example 85 wherein the first layer is a full convolutional layer, and wherein each subsequent layer is a depthwise separable layer having 3×3 convolutions.

87. The system of example 85 or 86 wherein one or more of the convolutional layers include one or more feature filters configured to extract one or more features from a region of units using a convolution, wherein the one or more filter features includes 1) one or more local features, (2) one or more global features, (3) one or more edges, (4) one or more colors, (5) one or more intensity level, (6) one or more spatial features, and/or (7) one or more shape features.

88. A computer-implemented method for training an artificial intelligence system to identify neutrophil extracellular traps in peripheral blood smears, the method comprising:
  receiving a plurality of inputs, wherein the plurality of inputs includes stained images of biological samples, and wherein each individual stained image is associated with a particular target output;
  receiving a plurality of observations corresponding to the plurality of inputs, wherein each observation includes the particular target output; and
  based on the plurality of inputs and the plurality of observations, training the artificial intelligence system to identify neutrophil extracellular traps in peripheral blood smears;
  wherein the artificial intelligence system includes a depthwise separable convolutional neural network.

89. The computer-implemented method of example 88 wherein the stained images include a first plurality of images and a second plurality of images, and wherein the first plurality of images includes images of a stained biological sample having neutrophil extracellular traps, and wherein the second plurality of images includes images of a stained biological sample without neutrophil extracellular traps.

90. The computer-implemented method of example 88 or 89 wherein the neural network includes a multi-layered architecture having between 3 and 40 layers.

91. The computer-implemented method of example 90 wherein the first layer is a full convolutional layer, and wherein each subsequent layer is a depthwise separable layer having 3×3 convolutions.

92. The method of example 90 or 91 wherein one or more of the convolutional layers include one or more feature filters configured to extract one or more features from a region of units using a convolution, and wherein the one or more features includes (1) one or more local features, (2) one or more global features, (3) one or more edges, (4) one or more colors, (5) one or more intensity level, (6) one or more spatial features, and/or (7) one or more shape features.

93. A non-transitory computer readable medium storing an artificial intelligence architecture, the artificial intelligence architecture comprising a depthwise separable convolutional neural network having between 3 layers and 40 layers, wherein the depthwise separable convolutional neural network is trained to analyze an image of a stained biological sample to identify neutrophil extracellular traps in the image.

94. The non-transitory computer readable medium of example 93 wherein the depthwise separable convolutional neural network includes a 28-layer architecture.

95. The non-transitory computer readable medium of example 93 or 94 wherein the first layer is a full convolutional layer, and wherein each subsequent layer is a depthwise separable layer having 3×3 convolutions.

96. The non-transitory computer readable medium of any of examples 93-95 wherein one or more of the convolutional layers include one or more feature filters configured to extract one or more features from a region of units using a convolution.

97. The non-transitory computer readable medium of example 96, wherein the one or more features includes (1) one or more local features, (2) one or more global features, (3) one or more edges, (4) one or more colors, (5) one or more intensity level, (6) one or more spatial features, and/or (7) one or more shape features.

98. The non-transitory computer readable medium of any of examples 93-97 wherein the neural network has a width multiplier α of 1.

99. The non-transitory computer readable medium of any of examples 93-97 wherein the neural network has a width multiplier α less than 1.

100. A system for identifying neutrophil extracellular traps in blood, the system comprising:
a computing device including one or more processors and a non-transitory computer readable medium storing (i) a data analysis module, and (ii) instructions that, when executed by the one or more processors, cause the computing device to perform operations comprising:
accessing a complete blood count (CBC) scattergram of a biological sample including blood;
analyzing, via the data analysis module, the CBC scattergram to identify one or more patterns in the CBC scattergram that indicate the presence or absence of NETs in the biological sample; and
indicating whether the biological sample includes neutrophil extracellular traps.

101. The system of claim 100 wherein the data analysis module includes an artificial intelligence architecture, and wherein analyzing the CBC scattergram includes using the artificial intelligence architecture to identify the one or more patterns in the CBC scattergram that indicate the presence or absence of NETs.

102. The system of claim 101 wherein the artificial intelligence architecture is a depthwise separable convolutional neural network.

103. The system of claim 100 wherein analyzing the CBC scattergram includes analyzing the fluorescence within a predetermined area on the CBC scattergram, and wherein the predetermined area is associated with neutrophil extracellular traps.

104. The system of claim 100 wherein the instructions, when executed, further cause the computing device to perform the operation of (i) indicating the total number of neutrophil extracellular traps identified in the dataset of images and/or (ii) indicating a ratio of neutrophil extracellular traps to other white blood cells.

Conclusion

The above detailed description of embodiments of the technology are not intended to be exhaustive or to limit the technology to the precise forms disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A computer-implemented method for identifying neutrophil extracellular traps in blood using a computing system, the method comprising:

obtaining one or more images of a biological sample, wherein the biological sample includes white blood cells;
sorting the one or more images into a first set of images containing smudge cells within the imaged white blood cells and a second set of images not containing smudge cells within the imaged white blood cells;
analyzing one or more morphological features of the smudge cells in the first set of images, wherein analyzing the one or more morphological features includes using an artificial intelligence architecture that includes a depthwise separable convolutional neural network; and
based at least in part on the analysis of the one or more morphological features, indicating whether the smudge cells include neutrophil extracellular traps.

2. The computer-implemented method of claim 1, further comprising generating a confidence score for each of the first set of images, wherein the confidence score reflects a likelihood that a particular image of the first set of images contains a neutrophil extracellular trap.

3. The computer-implemented method of claim 1, further comprising indicating whether the smudge cells include degenerating lymphocytes.

4. The computer-implemented method of claim 1, further comprising sorting the first set of images based at least in part on whether the first set of images include neutrophil extracellular traps.

5. The computer-implemented method of claim 1 wherein the one or more images comprises a dataset of images corresponding to a biological sample taken from a single subject.

6. The computer-implemented method of claim 5 wherein indicating whether the smudge cells include neutrophil extracellular traps further comprises (i) indicating the total number of neutrophil extracellular traps identified in the first set of images and/or (ii) indicating a ratio of neutrophil extracellular traps to other white blood cells.

7. The computer-implemented method of claim 1 wherein obtaining the one or more images includes receiving, from an automated imaging system, the one or more images.

8. The computer-implemented method of claim 1 wherein obtaining the one or more images includes directing an automated imaging system to take the one or more images.

9. The computer-implemented method of claim 1 wherein the depthwise separable convolutional neural network is trained to identify neutrophil extracellular traps based solely on morphology.

10. The computer-implemented method of claim 1 wherein the computing system is an automated imaging system, and wherein the automated imaging system includes one or more cameras configured to obtain the one or more images.

11. The computer-implemented method of claim 1 wherein the computing system is a mobile device, and wherein the mobile device includes one or more cameras configured to obtain the one or more images.

12. The computer-implemented method of claim 1 wherein the depthwise separable convolutional neural network includes a multi-layered architecture having between 3 and 40 layers.

13. The computer-implemented method of claim 12 wherein the first layer is a full convolutional layer, and wherein each subsequent layer is a depthwise separable layer having 3×3 convolutions.

14. The computer-implemented method of claim 12 wherein one or more of the convolutional layers include one or more feature filters configured to extract one or more features from a region of units using a convolution, wherein the one or more filter features includes 1) one or more local features, (2) one or more global features, (3) one or more edges, (4) one or more colors, (5) one or more intensity level, (6) one or more spatial features, and/or (7) one or more shape features.

15. A system for identifying neutrophil extracellular traps in peripheral blood smears, the system comprising:
a computing device including one or more processors and a non-transitory computer readable medium storing (i) a data analysis module including a depthwise separable convolutional neural network, and (ii) instructions that, when executed by the one or more processors, cause the computing device to perform operations comprising:
obtaining one or more images of a biological sample, wherein the biological sample includes white blood cells;
sorting the one or more images into a first set of images containing smudge cells within the imaged white blood cells and a second set of images not containing smudge cells within the imaged white blood cells;
analyzing, via the data analysis module, one or more morphological features of the smudge cells in the first set of images; and
based at least in part on the one or more analyzed morphological features of the smudge cells, indicating whether the smudge cells include neutrophil extracellular traps.

16. The system of claim 15 wherein the instructions, when executed, further cause the computing device to perform the operation of providing a confidence score for each of the first set of images, and wherein the confidence score reflects a likelihood that a particular image of the first set of images contains a neutrophil extracellular trap.

17. The system of claim 15 wherein the instructions, when executed, further cause the computing device to perform the operation of indicating whether the smudge cells include degenerating lymphocytes.

18. The system of claim 15 wherein the instructions, when executed, further cause the computing device to perform the operation of sorting the first set of images based at least in part on whether the first set of images include neutrophil extracellular traps.

19. The system of claim 15 wherein the instructions, when executed, further cause the computing device to perform the operation of (i) indicating the total number of neutrophil extracellular traps identified and/or (ii) indicating a ratio of neutrophil extracellular traps to other white blood cells.

20. The system of claim 15 wherein the depthwise separable convolutional neural network is pretrained to identify neutrophil extracellular traps based on morphology.

21. The method of claim 15 wherein the computing device is an automated imaging system, and wherein the automated imaging system includes one or more cameras configured to obtain the one or more images.

22. The method of claim 15 wherein the computing device is a mobile device, and wherein the mobile device is configured to obtain the one or more images.

23. A computer-implemented method for training an artificial intelligence system to identify neutrophil extracellular traps in peripheral blood smears, the method comprising:
receiving a plurality of inputs, wherein the plurality of inputs includes stained images of biological samples containing smudge cells, and wherein each individual stained image is associated with a particular target output of whether the smudge cells include neutrophil extracellular traps;

receiving a plurality of observations corresponding to the plurality of inputs, wherein each observation includes the particular target output; and based on the plurality of inputs and the plurality of observations, training the artificial intelligence system to identify neutrophil extracellular traps within smudge cells in peripheral blood smears;

wherein the artificial intelligence system includes a depthwise separable convolutional neural network.

24. The computer-implemented method of claim 23 wherein the stained images include a first plurality of images and a second plurality of images, and wherein the first plurality of images includes images of a stained biological sample having neutrophil extracellular traps within the smudge cells, and wherein the second plurality of images includes images of a stained biological sample without neutrophil extracellular traps within the smudge cells.

25. The computer-implemented method of claim 23 wherein the depthwise separable neural network includes a multi-layered architecture having between 3 and 40 layers.

26. The computer-implemented method of claim 25 wherein the first layer is a full convolutional layer, and wherein each subsequent layer is a depthwise separable layer having 3×3 convolutions.

27. The method of claim 25 wherein one or more of the layers include one or more feature filters configured to extract one or more features from a region of units using a convolution, and wherein the one or more features includes (1) one or more local features, (2) one or more global features, (3) one or more edges, (4) one or more colors, (5) one or more intensity level, (6) one or more spatial features, and/or (7) one or more shape features.

* * * * *